(12) United States Patent
Chackalamannil et al.

(10) Patent No.: US 7,888,369 B2
(45) Date of Patent: Feb. 15, 2011

(54) OXAZOLOISOQUINOLINE DERIVATIVES AS THROMBIN RECEPTOR ANTAGONISTS

(75) Inventors: Samuel Chackalamannil, Califon, NJ (US); Yuguang Wang, Monroe, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/642,170

(22) Filed: Dec. 20, 2006

(65) Prior Publication Data

US 2007/0149518 A1    Jun. 28, 2007

Related U.S. Application Data

(60) Provisional application No. 60/753,214, filed on Dec. 22, 2005.

(51) Int. Cl.
| C07D 491/14 | (2006.01) |
| A61K 31/4355 | (2006.01) |
| A61P 7/02 | (2006.01) |
| A61P 9/10 | (2006.01) |
| A61P 9/12 | (2006.01) |
| A61P 9/06 | (2006.01) |
| A61P 9/00 | (2006.01) |
| A61P 9/02 | (2006.01) |

(52) U.S. Cl. ............................ 514/291; 546/89
(58) Field of Classification Search ............. 514/291, 514/230.2; 546/89; 544/89
See application file for complete search history.

(56) References Cited

U.S. PATENT DOCUMENTS

| 5,362,738 | A | * | 11/1994 | Burner et al. | ........... 514/294 |
| 5,726,182 | A | * | 3/1998 | Chu et al. | ............ 514/291 |
| 6,063,847 | A | | 5/2000 | Chackalamannil et al. | |
| 6,326,380 | B1 | | 12/2001 | Chackalamannil et al. | |
| 6,433,177 | B1 | * | 8/2002 | Bellani et al. | ........... 546/146 |
| 6,645,987 | B2 | | 11/2003 | Chackalamannil et al. | |
| 7,037,920 | B2 | | 5/2006 | Chackalamannil et al. | |
| 2001/0009916 | A1 | * | 7/2001 | Romero | ............. 514/292 |
| 2002/0045623 | A1 | * | 4/2002 | Charrier et al. | .......... 514/249 |
| 2004/0152736 | A1 | | 8/2004 | Chackalamannil et al. | |

FOREIGN PATENT DOCUMENTS

WO    WO 01/96330 A2    12/2001

OTHER PUBLICATIONS

Bensaid et al., "The Cannabinoid $CB_1$ Receptor Antagonist SR141716 Increases Acrp30 mRNA Expression in Adipose Tissue of Obese fa/fa Rats and in Cultured Adipocyte Cells", Molecular Pharmacology, 63(4): 908-914 (2003).
Bernatowicz et al., "Development of Potent Thrombin Receptor Antagonist Peptides", *J. Med. Chem.*, 39: 4879-4887 (1996).
Chackalamannil, "A Highly Efficient Total Synthesis of (+)-Himbacine", *J. Am. Chem. Soc.*, 118: 9812-9813 (1996).
Pertwee, "Pharmacology of Cannabinoid Receptor Ligands", *Current Medicinal Chemistry*, 6(8): 635-664 (1999).
International Search Report dated Dec. 5, 2007 for corresponding PCT Application No. PCT/US2006/048646.

* cited by examiner

*Primary Examiner*—James O Wilson
*Assistant Examiner*—Cecilia M Jaisle
(74) *Attorney, Agent, or Firm*—Mark W. Russell

(57) ABSTRACT

This application provides for oxazolisoquinoline derivatives of the formula

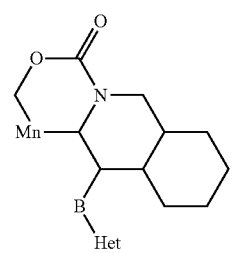

or a pharmaceutically acceptable salt of said compound wherein:
B is —CH=CH—;
M is —C(R$^1$)(R$^2$)—; and
the remaining substituents are as defined in the specification as well as pharmaceutical compositions containing them and a method of treating diseases associated with thrombosis, atherosclerosis, restenosis, hypertension, angina pectoris, arrhythmia, heart failure, and cancer by administering said compounds. This application also provides for combination therapy with the compounds of Ib or pharmaceutically acceptable salts thereof with other cardiovascular agents.

8 Claims, No Drawings

OXAZOLOISOQUINOLINE DERIVATIVES AS THROMBIN RECEPTOR ANTAGONISTS

This application claims the benefit of U.S. Provisional Application No. 60/753,214, filed Dec. 22, 2005, which is incorporated by reference herein in its entirety.

BACKGROUND OF THE INVENTION

The present invention relates to himbacine derivatives, which can be useful as thrombin receptor antagonists in the treatment of diseases associated with thrombosis, atherosclerosis, restenosis, hypertension, angina pectoris, arrhythmia, heart failure, cerebral ischemia, stroke, neurodegenerative diseases and cancer. Thrombin receptor antagonists are also known as protease activated receptor-1 (PAR-1) antagonists. The compounds of the invention also can be useful as cannabinoid ($CB_2$) receptor inhibitors for the treatment of rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis. The invention also relates to pharmaceutical compositions comprising said compounds.

Thrombin is known to have a variety of activities in different cell types. Thrombin receptors are known to be present in such cell types as human platelets, vascular smooth muscle cells, endothelial cells and fibroblasts. It is therefore expected that thrombin receptor antagonists will be useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al., *J. Med. Chem.*, 39 (1996), p. 4879-4887, tetra- and pentapeptides are disclosed as being potent thrombin receptor antagonists, for example N-trans-cinnamoyl-p-fluoroPhe-p-guanidinoPhe-Leu-Arg-NH$_2$ and N-trans-cinnamoyl-p-fluoroPhe-p-guanidinoPhe-Leu-Arg-Arg-NH$_2$. Peptide thrombin receptor antagonists are also disclosed in WO 94/03479, published Feb. 17, 1994.

Cannabinoid receptors belong to the superfamily of G-protein coupled receptors. They are classified into the predominantly neuronal $CB_1$ receptors and the predominantly peripheral $CB_2$ receptors. These receptors exert their biological actions by modulating adenylate cyclase and $Ca^{+2}$ and $K^+$ currents. While the effects of $CB_1$ receptors are principally associated with the central nervous system, $CB_2$ receptors are believed to have peripheral effects related to bronchial constriction, immunomodulation and inflammation. As such, a selective $CB_2$ receptor binding agent is expected to have therapeutic utility in the control of diseases associated with rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis (R. G. Pertwee, *Curr. Med. Chem.* 6(8), (1999), 635; M. Bensaid, *Molecular Pharmacology*, 63 (4), (2003), 908.).

Himbacine, a piperidine alkaloid of the formula

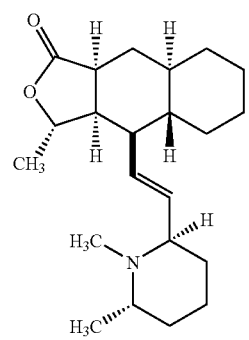

has been identified as a muscarinic receptor antagonist. The total synthesis of (+)-himbacine is disclosed in Chackalamannil et al., *J. Am. Chem. Soc.*, 118 (1996), p. 9812-9813.

Substituted tricyclic thrombin receptor antagonists are disclosed in U.S. Pat. No. 6,063,847, U.S. Pat. No. 6,326,380, U.S. Pat. No. 6,645,987 (WO 01/96330) and U.S. Ser. No. 10/271,715.

SUMMARY OF THE INVENTION

The present invention relates to compounds represented by the formula I:

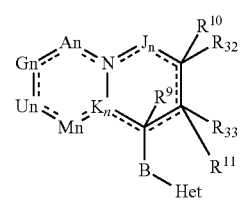

or a pharmaceutically acceptable salt, solvate, or ester of said compound, wherein ----- represents a double bond or a single bond, as permitted by the valency requirement; with the proviso that $R^{10}$ or $R^{11}$ are absent when the carbon to which $R^{10}$ or $R^{11}$ are attached is part of a double bond;

B is $-(CH_2)_{n3}-$, $-(CH_2)-O-$, $-(CH_2)S-$, $-(CH_2)-NR^6-$, $-C(O)NR^6-$, $-NR^6C(O)-$,

$-(CH_2)_{n4}CR^{12}=CR^{12a}(CH_2)_{n5}-$ or $-(CH_2)_{n4}C\equiv C(CH_2)_{n5}-$, wherein $n_3$ is 0-5, $n_4$ and $n_5$ are independently 0-2, and $R^{12}$ and $R^{12a}$ are independently selected from the group consisting of hydrogen, $C_1$-$C_6$ alkyl and halogen;

A, G, J, M and U are independently selected from the group consisting of $-N(R^{54})-$, $-(CR^1R^2)-$, $-O-$,

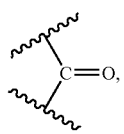

—S—,
—S(O)—,
—S(O)$_2$— and

with the provisos that selection of A, G, U, J, and M does not result in adjacent oxygen or sulfur atoms and that at least one carbon atom appear between any oxygen, nitrogen or sulfur atoms;

each n is independently 0, 1 or 2 with the provisos that all n variables cannot be simultaneously 0 and that the total of n variables cannot be greater than 7;

K is selected from the group consisting of

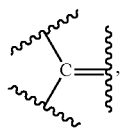

—CR$^1$—, and —N—;

Het is a mono-, bi- or tricyclic heteroaromatic group of 5 to 14 atoms comprised of 1 to 13 carbon atoms and 1 to 4 heteroatoms independently selected from the group consisting of N, O and S, with the proviso that there are no adjacent oxygen or sulfur atoms present in the heteroaromatic group, wherein a ring nitrogen can form an N-oxide or a quaternary group with an alkyl group, wherein Het is attached to B by a carbon atom ring member, and wherein the Het group is substituted by 1 to 4 moieties, W, wherein each W is independently selected from the group consisting of hydrogen, alkyl, fluoroalkyl, difluoroalkyl, trifluoroalkyl, haloalkyl, dihaloalkyl, trihaloalkyl, cycloalkyl, cycloalkyl substituted by alkyl, alkenyl, or alkynyl, heterocycloalkyl, heterocycloalkyl substituted by alkyl, alkenyl, or alkynyl, R$^{21}$-arylalkyl, R$^{21}$-aryl-alkenyl, heteroaryl, heteroarylalkyl, heteroarylalkenyl, hydroxyalkyl, dihydroxyalkyl, aminoalkyl, alkylaminoalkyl, di-(alkyl)-aminoalkyl, thioalkyl, alkoxy, alkenyloxy, halogen,

—NR$^4$R$^5$,

—SH,

—CN,

—OH,

—C(O)OR$^{17}$, —COR$^{16}$, —OS(O$_2$)CF$_3$, —CH$_2$OCH$_2$CF$_3$, alkylthio,

—C(O)NR$^4$R$^5$,

—OCHR$^6$-phenyl, phenoxyalkyl,

—NHCOR$^{16}$,

—NHSO$_2$R$^{16}$, biphenyl,

—OC(R$^6$)$_2$COOR$^7$, —OC(R$^6$)$_2$C(O)NR$^4$R$^5$, alkoxy substituted by alkyl, amino or —NHC(O)OR$^{17}$, aryl, aryl substituted by 1 to 3 substituents independently selected from the group consisting of alkyl, halogen, alkoxy, methylenedioxy, carboxylic acid, carboxamide, amine, urea, amide, sulfonamide, —CN, —CF$_3$, —OCF$_3$, —OH, alkylamino-, di-(alkyl)amino-, —NR$^{25}$R$^{26}$alkyl-, hydroxyalkyl-, —C(O)OR$^{17}$, —COR$^{17}$, —NHCOR$^{16}$, —NHS(O)$_2$R$^{16}$, —NHS(O)$_2$CH$_2$CF$_3$, —C(O)NR$^{25}$R$^{26}$, —NR$^{25}$—C(O)—NR$^{25}$R$^{26}$, —S(O)R$^{13}$, —S(O)$_2$R$^{13}$ and

—SR$^{13}$, or alkyl optionally substituted with —NR$^1$R$^2$, —NR$^1$COR$^2$, —NR$^1$CONR$^1$R$^2$, —NR$^1$C(O)OR$^2$, —NR$^1$S(O)$_2$R$^2$, —NR$^1$S(O)$_2$NR$^1$R$^2$, —C(O)OH, —C(O)OR$^1$, —CONR$^1$R$^2$heteroaryl, hydroxyalkyl, alkyl, —S(O$_2$-alkyl, —C(O)NR$^4$R$^5$ or heteroaryl;

wherein adjacent carbons on the Het ring can optionally form a ring with a methylenedioxy group;

R$^1$ and R$^2$ are independently selected from the group consisting of hydrogen, halogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, amine, aminoalkyl, aryl, thiohydroxy, CN, and thioalkyl; or R$^1$ and R$^2$ when attached to nitrogen, taken together, form a mono or bicyclic heterocyclic ring of 4 to 10 atoms, with 1-3 heteroatoms selected from —O—, —N—, —S—, —S(O)—, —S(O)$_2$— and

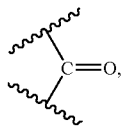

with the proviso that S and O ring atoms are not adjacent to each other, where said heterocyclic ring is unsubstituted or substituted with one or more groups independently selected from alkyl, halogen, hydroxy, alkoxy, aryloxy and arylalkoxy;

R$^6$ is hydrogen, alkyl or phenyl;

R$^7$ is hydrogen or alkyl;

R$^{16}$ and R$^{16a}$ are independently selected from the group consisting of hydrogen, alkyl, phenyl and benzyl;

$R^{16b}$ is hydrogen, alkoxy, alkyl, alkoxyalkyl-, $R^{22}$—O—C(O)-alkyl-, cycloalkyl, $R^{21}$-aryl, $R^{21}$-arylalkyl, haloalkyl, alkenyl, halo substituted alkenyl, alkynyl, halo substituted alkynyl, $R^{21}$-heteroaryl, ($R^{21}$-heteroaryl)-alkyl-, ($R^{21}$-heterocycloalkyl)-alkyl-, $R^{28}R^{29}$N-alkyl-, $R^{28}R^{29}$N—C(O)-alkyl-, $R^{28}R^{29}$N—C(O)O-alkyl-, $R^{28}$OC(O)N($R^{29}$)-alkyl-, $R^{28}$S(O)$_2$N($R^{29}$)-alkyl-, $R^{28}R^{29}$N—C(O)—N($R^{29}$)-alkyl-, $R^{28}R^{29}$N—S(O)$_2$N($R^{29}$)-alkyl-, $R^{28}$—C(O)N($R^{29}$)-alkyl-, $R^{28}R^{29}$N—S(O)$_2$-alkyl-, HOS(O)$_2$-alkyl-, (OH)$_2$P(O)$_2$-alkyl-, $R^{28}$—S-alkyl-, $R^{28}$—S(O)$_2$-alkyl-, or hydroxyalkyl;

$R^{17}$ is selected from the group consisting of hydrogen, alkyl, phenyl and benzyl;

$R^{18}$ and $R^{19}$ are hydrogen, alkyl, aryl, $R^{21}$-aryl, heteroaryl, cycloalkyl, heterocyclyl, alkoxyalkyl, haloalkoxyalkyl, aryloxyalkyl, arylalkoxyalkyl, heteroaryloxyalkyl, heteroarylalkoxyalkyl, cycloalkyloxyalkyl, (heterocyclyl)alkyloxyalkyl, alkoxyalkyloxyalkyl, —S(O)$_2$-alkyl, —C(NH)NR$^1$R$^2$ or alkyl substituted with one or two moieties independently selected from the group consisting of cycloalkyl, halogen, hydroxy, —NR$^1$R$^2$, —NR$^1$C(O)R$^2$, —NR$^1$C(O)NR$^1$R$^2$, —NR$^1$C(O)OR$^2$, —NR$^1$S(O)$_2$R$^2$, —NR$^1$S(O)$_2$NR$^1$R$^2$, —C(O)OH, —C(O)OR$^1$ and —C(O)NR$^1$R$^2$;

or $R^{18}$ and $R^{19}$ together with the nitrogen to which they are attached, form a mono or bicyclic heterocyclic ring of 4 to 10 atoms, having 1-3 hetero ring atoms selected from the group consisting of —O—, —N—, —S—, —S(O)—, —S(O)$_2$— and

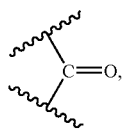

with the proviso that S and O atoms are not adjacent to each other, the ring being unsubstituted or substituted with one or more groups independently selected from alkyl, halogen, hydroxy, alkoxy, aryloxy, arylalkoxy, —NR$^1$R$^2$, —NR$^1$COR$^2$, —NR$^1$C(O)NR$^1$R$^2$, —NR$^1$C(O)OR$^2$, —NR$^1$S(O)$_2$R$^2$, —NR$^1$S(O)$_2$NR$^1$R$^2$, —C(O)OR$^1$, —CONR$^1$R$^2$ and alkyl substituted with —NR$^1$R$^2$, —NR$^1$COR$^2$, —NR$^1$CONR$^1$R$^2$, —NR$^1$C(O)OR$^2$, —NR$^1$S(O)$_2$R$^2$, —NR$^1$S(O)$_2$NR$^1$R$^2$, —C(O)OR$^1$ or —CONR$^1$R$^2$;

$R^{21}$ is 1 to 3 moieties and each $R^{21}$ is independently selected from the group consisting of hydrogen, —CN, —CF$_3$, —OCF$_3$, halogen, —NO$_2$, alkyl, —OH, alkoxy, alkylamino-, di-(alkyl)amino-, —NR$^{25}$R$^{26}$alkyl-, hydroxyalkyl-, —C(O)OR$^{17}$, —COR$^{17}$, —NHCOR$^{16}$, —NHS(O)$_2$R$^{16}$, —C(NH)—NH$_2$, —NHS(O)$_2$CH$_2$CF$_3$, —C(O)NR$^{25}$R$^{26}$, —NR$^{25}$—C(O)—NR$^{25}$R$^{26}$, —S(O)R$^{16}$, —S(O)$_2$R$^{16}$, —SR$^{16}$, —SO$_2$NR$^4$R$^5$ and —CONR$^4$R$^5$;

or two adjacent $R^{21}$ moieties can form a methylenedioxy group;

$R^{22}$ is hydrogen, alkyl, phenyl, benzyl, —COR$^{16}$, —CONR$^{18}$R$^{19}$, —COR$^{23}$, —S(O)R$^{31}$, —S(O)$_2$R$^{31}$, —S(O)$_2$NR$^{24}$R$^{25}$ or —C(O)OR$^{27}$;

$R^{23}$ is

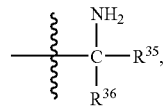

wherein $R^{35}$ and $R^{36}$ are independently selected from the group consisting of hydrogen, alkyl, and $R^{37}$-substituted alkyl, wherein $R^{37}$ is selected from the group consisting of HO—, HS—, CH$_2$S—, —NH$_2$, phenyl, p-hydroxyphenyl and indolyl;

or $R^{23}$ is alkyl, haloalkyl, alkenyl, haloalkenyl, alkynyl, cycloalkyl, cycloalkylalkyl, cycloalkyl substituted by 1 to 3 substituents independently selected from the group consisting of alkoxyalkyl, alkyl, halogen, hydroxy, alkoxy, aryloxy, arylalkoxy, —NR$^1$R$^2$, —NR$^1$C(O)R$^2$, —NR$^1$C(O)NR$^1$R$^2$, —NR$^1$C(O)OR$^2$, —NR$^1$S(O)$_2$R$^2$, —NR$^1$S(O)$_2$NR$^1$R$^2$, —C(O)OH, —C(O)OR$^1$ and —CONR$^1$R$^2$, aryl, aralkyl, heteroaryl, heterocycloalkyl, or alkyl substituted with —NR$^1$R$^2$, —NR$^1$COR$^2$, —NR$^1$CONR$^1$R$^2$, —NR$^1$C(O)OR$^2$, —NR$^1$S(O)$_2$R$^2$, —NR$^1$S(O)$_2$NR$^1$R$^2$, —C(O)OH, —C(O)OR$^1$, —CONR$^1$R$^2$ or —SO$_3$H;

$R^{24}$, $R^{25}$ and $R^{26}$ are independently selected from the group consisting of hydrogen, alkyl, haloalkyl, alkenyl, alkynyl, aryl, aralkyl, cycloalkyl, halocycloalkyl, alkoxyalkyl, hydroxy and alkoxy;

$R^{27}$ is 1 to 3 moieties and each $R^{27}$ is independently selected from the group consisting of hydrogen, alkyl, and cycloalkyl, wherein when $R^{27}$ is alkyl or cyloalkyl, $R^{27}$ is optionally substituted with —OH, —C(O)OH, halogen or alkoxy;

$R^{28}$ and $R^{29}$ are independently selected from the group consisting of hydrogen, alkyl, alkoxy, arylalkyl, heteroaryl, heteroarylalkyl, hydroxyalkyl, alkoxyalkyl, heterocyclyl, heterocyclylalkyl, and haloalkyl; or $R^{28}$ and $R^{29}$ taken together form a spirocyclic or a heterospirocyclic ring having 3-6 ring atoms;

$R^{32}$ and $R^{33}$ are independently selected from the group consisting of hydrogen, $R^{34}$-alkyl, $R^{34}$-alkenyl, $R^{34}$-alkynyl, $R^{40}$-heterocycloalkyl, $R^{38}$-aryl, $R^{38}$-aralkyl, $R^{42}$-cycloalkyl, $R^{42}$-cycloalkenyl, —OH, —OC(O)R$^{43}$, —C(O)OR$^{43}$, —C(O)R$^{43}$, —C(O)NR$^{43}$R$^{44}$, —NR$^{43}$R$^{44}$, —NR$^{43}$C(O)R$^{44}$, —NR$^{43}$C(O)NR$^{44}$R$^{45}$, —NHS(O)$_2$R$^{43}$, —OC(O)NR$^{43}$R$^{44}$, $R^{37}$-alkoxy, $R^{37}$-alkenyloxy, $R^{37}$-alkynyloxy, $R^{40}$-heterocycloalkyloxy, $R^{42}$-cycloalkyloxy, $R^{42}$-cyclo-alkenyloxy, $R^{42}$-cycloalkyl-NH—, —NHSO$_2$NHR$^{16}$ and —CH(=NOR$^{17}$);

or $R^{32}$ and $R^{10}$ together with the carbon to which they are attached, or $R^{33}$ and $R^{11}$ together with the carbon to which they are attached, independently form a $R^{42}$-substituted carbocyclic ring of 3-10 atoms;

or a $R^{42}$-substituted heterocyclic ring of 4-10 atoms wherein 1-3 ring members are independently selected from the group consisting of —O—, —NH— and —SO$_{0-2}$—, provided that when $R^{32}$ and $R^{10}$ form a ring, or $R^{33}$ and $R^{11}$ form a ring the optional double bond is absent;

$R^{42}$ is 1 to 3 substituents independently selected from the group consisting of hydrogen, —OH, (C$_1$-C$_6$)alkyl, (C$_1$-C$_6$)alkoxy, NH$_2$, and halogen;

or $R^{32}$ and $R^{33}$ are combined to form a ring structure Q, below

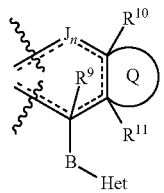

where $R^9$ is hydrogen, OH, (C$_1$-C$_6$)alkoxy, halogen, halo(C$_1$-C$_6$)alkyl, amine, thiohydroxy, (C$_1$-C$_6$)alkyl, or CN;

Q is fused R-substituted aryl, R-substituted heteroaryl, R-substituted heterocyclic ring of 4-8 atoms containing 1-3 heteroatoms independently selected from O, S, S(O), S(O)$_2$ and NR$^{22}$ with the proviso that S and O cannot be adjacent to one another; or Q is

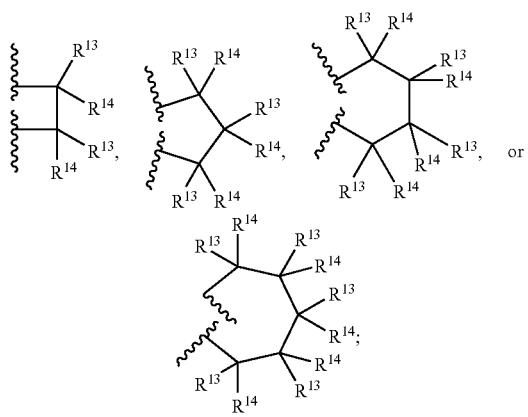

wherein each $R^{13}$ is independently selected from hydrogen, alkyl, cycloalkyl, haloalkyl, halogen, —(CH$_2$)$_{n6}$NHC(O)OR$^{16b}$, —(CH$_2$)$_{n6}$NHC(O)R$^{16b}$, —(CH$_2$)$_{n6}$NHC(O)NR$^4$R$^5$, —(CH$_2$)$_{n6}$NHSO$_2$R$^{16}$, —(CH$_2$)$_{n6}$NHSO$_2$NR$^4$R$^5$, and —(CH$_2$)$_{n6}$C(O)NR$^{28}$R$^{29}$, where n$_6$ is 0-4;

each $R^{14}$ is independently selected from the group consisting of hydrogen, alkyl, —OH, alkoxy, arylalkyl, heteroaryl, heteroarylalkyl, heterocyclyl, heterocyclylalkyl, halogen, haloalkyl, —(CH$_2$)$_{n6}$NHC(O)OR$^{16b}$, —(CH$_2$)$_{n6}$NHC(O)R$^{16b}$, —(CH$_2$)$_{n6}$NHC(O)NR$^4$R$^5$, —(CH$_2$)$_{n6}$NHSO$_2$R$^{16}$, —(CH$_2$)$_{n6}$NHSO$_2$NR$^4$R$^5$, and —(CH$_2$)$_{n6}$C(O)NR$^{28}$R$^{29}$ where n$_6$ is 0-4; where $R^4$ and $R^5$ are independently selected from the group consisting of hydrogen, alkyl, phenyl, benzyl and cycloalkyl, or $R^4$ and $R^5$ together can form a ring with the nitrogen to which they are attached, wherein said ring formed by $R^4$ and $R^5$ is optionally substituted with =O, —OH, —OR$^1$ or

—C(O)OH;

or $R^{13}$ and $R^{14}$ taken together form a spirocyclic or a heterospirocyclic ring of 3-6 ring atoms, wherein said heterospirocyclic ring contains 2 to 5 carbon ring atoms and 1 or 2 hetero ring atoms selected from the group consisting of O, S and N;

wherein $R^{10}$ and $R^{11}$ are independently selected from the group consisting of R$^1$ and —OR$^1$, provided that when ring Q is aromatic and the carbon atoms bearing $R^{10}$ and $R^{11}$ are connected by a double bond, $R^{10}$ and $R^{11}$ are absent; or R is 1 to 5 moieties and each R is independently selected from the group consisting of hydrogen, alkyl, halogen, hydroxy, amine, alkylamino, dialkylamino, alkoxy, —COR$^{16}$, —C(O)OR$^{17}$, —C(O)NR$^4$R$^5$, —SOR$^{16}$, —S(O$_2$)R$^{16}$, —NR$^{16}$COR$^{16a}$, —NR$^{16}$C(O)OR$^{16a}$, —NR$^{16}$CONR$^4$R$^5$, —NR$^{16}$S(O$_2$)NR$^4$R$^5$, fluoroalkyl, difluoroalkyl, trifluoroalkyl, cycloalkyl, alkenyl, arylalkyl, arylalkenyl, heteroarylalkyl, heteroarylalkenyl, hydroxyalkyl, aminoalkyl, aryl, thiohydroxy, CN and thioalkyl;

$R^{34}$ is 1 to 3 moieties and each $R^{34}$ is independently selected from the group consisting of hydrogen, halogen, —OH, alkoxy, R$^{47}$-aryl, alkyl-C(O)—, alkenyl-C(O)—, alkynyl-C(O)—, heterocycloalkyl, R$^{39}$-cycloalkyl, R$^{39}$-cycloalkenyl, —OC(O)R$^{43}$, —C(O)R$^{43}$, —C(O)R$^{43}$, —C(O)NR$^{43}$R$^{44}$, —NR$^{43}$R$^{44}$, —NR$^{43}$C(O)R$^{44}$, —NR$^{43}$C(O)NR$^{44}$R$^{45}$, —NHSO$_2$R$^{43}$, —OC(O)NR$^{43}$R$^{44}$, R$^{39}$-alkenyloxy, R$^{39}$-alkynyloxy, R$^{40}$-heterocycloalkyloxy, R$^{42}$— cycloalkyloxy, R$^{42}$-cycloalkenyloxy, R$^{42}$-cycloalkyl-NH—, —NHSO$_2$NHR$^{16}$ and

—CH(=NOR$^{17}$);

$R^{38}$ is 1 to 3 moieties and each $R^{38}$ is independently selected from the group consisting of hydrogen, heterocycloalkyl, halogen, —C(O)OR$^{48}$, —CN, —C(O)NR$^{49}$R$^{50}$, —NR$^{51}$C(O)R$^{52}$, —OR$^{48}$, cycloalkyl, cycloalkylalkyl, alkylcycloalkylalkyl, haloalkylcycloalkylalkyl, hydroxyalkyl, alkoxyalkyl, and R$^{52}$-heteroaryl; or two $R^{38}$ groups on adjacent ring carbons form a fused methylenedioxy group;

$R^{39}$ is 1 to 3 moieties and each $R^{39}$ is independently selected from the group consisting of hydrogen, halogen and alkoxy;

$R^{40}$ is 1 to 3 moieties and each $R^{40}$ is independently selected from the group consisting of hydrogen, R$^{41}$-alkyl, R$^{41}$-alkenyl and R$^{41}$-alkynyl;

$R^{41}$ is hydrogen, —OH or alkoxy;

$R^{42}$ is 1 to 3 moieties and each $R^{42}$ is independently selected from the group consisting of hydrogen, alkyl, —OH, alkoxy and halogen;

$R^{43}$, $R^{44}$ and $R^{45}$ are independently selected from the group consisting of hydrogen, alkyl, alkoxyalkyl, R$^{38}$-arylalkyl, R$^{46}$-cycloalkyl, R$^{53}$-cycloalkylalkyl, R$^{38}$-aryl, heterocycloalkyl, heteroaryl, heterocycloalkylalkyl and heteroarylalkyl;

$R^{46}$ is hydrogen, alkyl, hydroxyalkyl or alkoxy;

$R^{47}$ is 1 to 3 moieties and each $R^{47}$ is independently selected from the group consisting of hydrogen, alkyl, —OH, halogen, —CN, alkoxy, trihaloalkoxy, alkylamino, di(alkyl) amino, —OCF$_3$, hydroxyalkyl, —CHO, —C(O)alkylamino, —C(O)di(alkyl)amino, —NH$_2$, —NHC(O)alkyl and —N(alkyl)C(O)alkyl;

$R^{48}$ is hydrogen, alkyl, haloalkyl, dihaloalkyl or trifluoroalkyl;

$R^{49}$ and $R^{50}$ are independently selected from the group consisting of hydrogen, alkyl, aralkyl, phenyl and cycloalkyl, or $R^{49}$ and $R^{50}$ together are —(CH$_2$)$_4$—, —(CH$_2$)$_5$— or —(CH$_2$)$_2$—NR$^{39}$—(CH$_2$)$_2$— and form a ring with the nitrogen to which they are attached;

$R^{51}$ and $R^{52}$ are independently selected from the group consisting of hydrogen, alkyl, aralkyl, phenyl and cycloalkyl, or $R^{51}$ and $R^{52}$ in the group —NR$^{39}$C(O)R$^{40}$, together with the nitrogen atoms to which they are attached, form a cyclic lactam having 5-8 ring members;

$R^{53}$ is hydrogen, alkoxy, —SOR$^{16}$, —SO$_2$R$^{17}$, —C(O)OR$^{17}$, —C(O)NR$^{18}$R$^{19}$, alkyl, halogen, fluoroalkyl, difluoroalkyl, trifluoroalkyl, cycloalkyl, alkenyl, aralkyl, arylalkenyl, heteroarylalkyl, heteroarylalkenyl, hydroxyalkyl, aminoalkyl, aryl, thioalkyl, alkoxyalkyl or alkylaminoalkyl; and $R^{54}$ is selected from the group consisting of hydrogen, alkyl, fluoroalkyl, difluoroalkyl, trifluoroalkyl, cycloalkyl, cycloalkyl substituted by 1 to 3 substituents selected from the group consisting of alkoxyalkyl, alkyl, halogen, hydroxy, alkoxy, aryloxy, arylalkoxy, —NR$^1$R$^2$, —NR$^1$C(O)R$^2$, —NR$^1$C(O)NR$^1$R$^2$, —NR$^1$C(O)OR$^2$, —NR$^1$S(O)$_2$R$^2$, —NR$^1$S(O)$_2$NR$^1$R$^2$, —C(O)OH, —C(O)OR$^1$ and —CONR$^1$R$^2$, alkenyl, alkoxy, arylalkyl, arylalkenyl, heteroarylalkyl, heteroarylalkenyl, hydroxyl, alkoxy, hydroxyalkyl, alkoxyalkyl, aminoalkyl, aryl, heteroaryl, thioalkyl, and alkyl substituted by 1 to 3 substituents independently selected from the group consisting of urea, sulfonamide, carboxamide, carboxylic acid, carboxylic ester and sulfonyl urea.

Pharmaceutical compositions comprising at least one compound of formula I and a pharmaceutically acceptable carrier are also provided. The compounds of the present invention can be useful as Thrombin receptor antagonists or PAR-1 antagonists for the treatment of a cardiovascular or circulatory disease or condition, an inflammatory disease or condition, a respiratory tract or disease or condition, cancer, acute renal failure, astrogliosis, a fibrotic disorder of the liver, kidney, lung or intestinal tract, Alzheimer's disease, diabetes, diabetic neuropathy, rheumatoid arthritis, neurodegenerative disease, neurotoxic disease, systemic lupus erythematosus, multiple sclerosis, osteoporosis, glaucoma, macular degeneration, psoriasis, radiation fibrosis, endothelial dysfunction, a wound or a spinal cord injury, or a symptom or result thereof.

Thrombin receptor antagonist compounds of the present invention can have anti-thrombotic, anti-platelet aggregation, anti-atherosclerotic, anti-restenotic and/or anti-coagulant activity. Thrombosis-related diseases treated by the compounds of this invention include thrombosis, atherosclerosis, restenosis, hypertension, angina pectoris, arrhythmia, heart failure, myocardial infarction, glomerulonephritis, thrombotic and thromboembolytic stroke, peripheral vascular diseases, other cardiovascular diseases, cerebral ischemia, inflammatory disorders and cancer, as well as other disorders in which thrombin and its receptor play a pathological role.

Certain embodiments of this invention also relate to a method of using at least one compound of Formula I in combination with one or more additional cardiovascular agents. Such combinations can be useful for the treatment of thrombosis, atherosclerosis, restenosis, hypertension, angina pectoris, angiogenesis related disorders, arrhythmia, a cardiovascular or circulatory disease or condition, heart failure, myocardial infarction, glomerulonephritis, thrombotic stroke, thromboembolytic stroke, peripheral vascular diseases, cerebral ischemia, rheumatoid arthritis, rheumatism, astrogliosis, a fibrotic disorder of the liver, kidney, lung or intestinal tract, systemic lupus erythematosus, multiple sclerosis, osteoporosis, glomerulonephritis, renal disease, acute renal failure, chronic renal failure, renal vascular homeostasis, renal ischemia, bladder inflammation, diabetes, diabetic neuropathy, cerebral stroke, cerebral ischemia, nephritis, cancer, melanoma, renal cell carcinoma, neuropathy and/or malignant tumors, neurodegenerative and/or neurotoxic diseases, conditions, or injuries, inflammation, asthma, glaucoma, macular degeneration, psoriasis, endothelial dysfunction disorders of the liver, kidney or lung inflammatory disorders of the lungs and gastrointestinal tract, respiratory tract disease or condition, radiation fibrosis, endothelial dysfunction, periodontal diseases or wounds or a spinal cord injury, or a symptom or result thereof. It is contemplated that a combination of this invention may be useful in treating more than one of the diseases listed.

Pharmaceutical compositions comprising a therapeutically effective amount of a combination of at least one compound of formula I and at least one additional cardiovascular agent in a pharmaceutically acceptable carrier are also provided.

It is further contemplated that the combination of the invention can be provided as a kit comprising in a single package at least one compound of formula I in a pharmaceutical composition, and at least one separate pharmaceutical composition comprising a cardiovascular agent.

DETAILED DESCRIPTION

In one embodiment, the present invention provides compounds represented by structural formula I, or pharmaceutically acceptable salt, solvate, or ester thereof, wherein the various moieties are as described as above.

For compounds of Formula I, embodiments of the compounds of formula I are as follows:
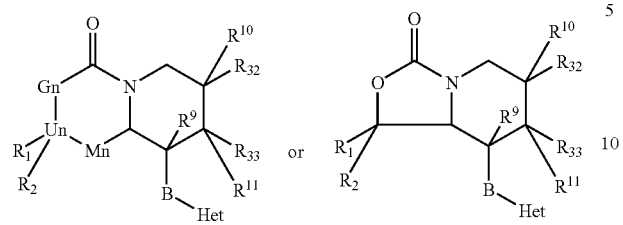
Additional embodiments of the compounds of formula I are as follows:
Ia
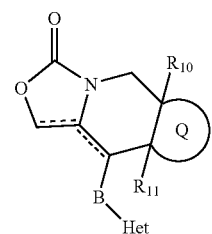
IIa
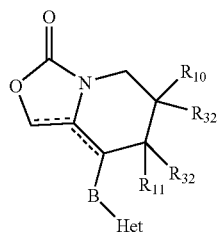
Ib
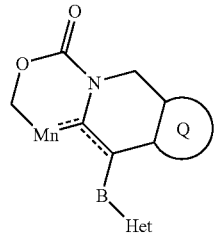
IIb
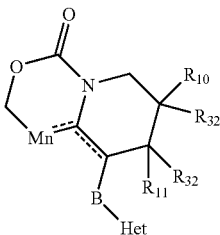
Ic
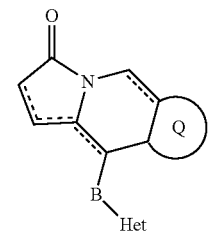
IIc
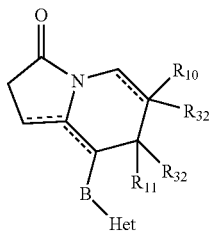
Id
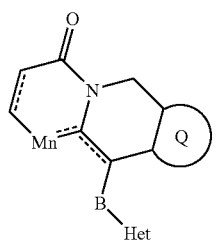
IId
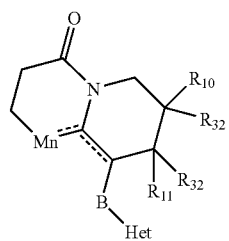
Ie
IIe
If
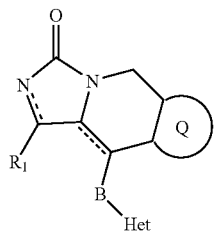

-continued
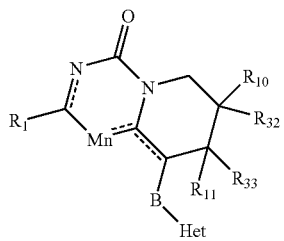
IIf
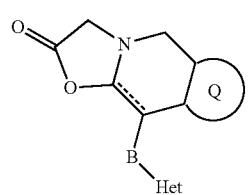
Ig
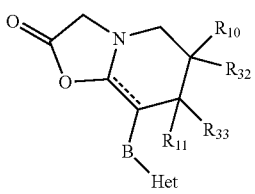
Ig
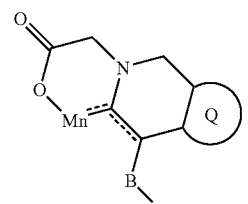
Ih
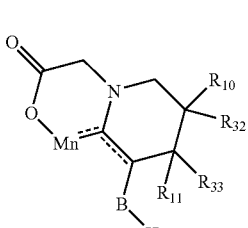
IIh
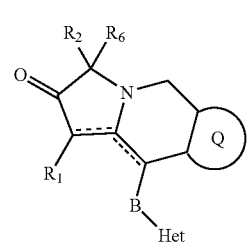
Ii
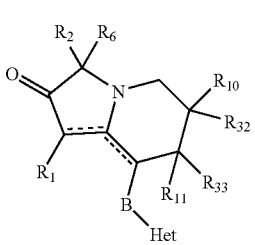
IIi
-continued
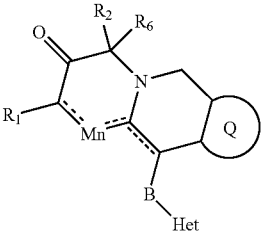
Ij
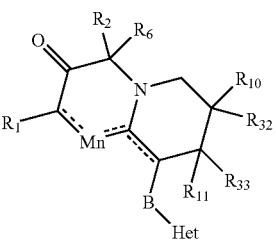
IIj
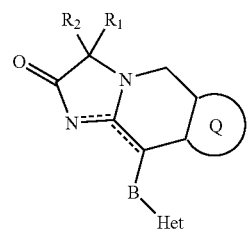
Ik
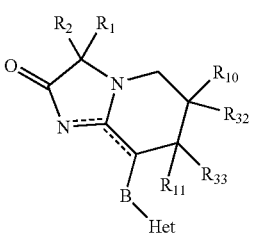
IIk
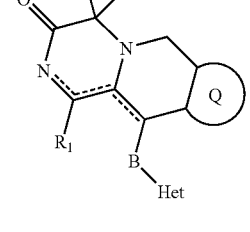
Il
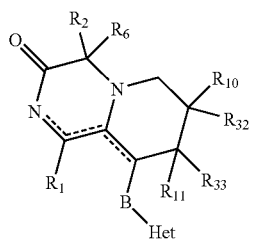
IIl -continued

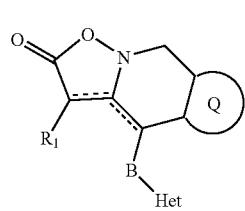
Im

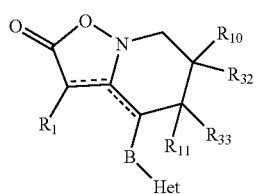
IIm

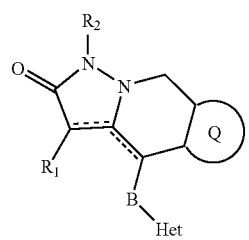
In

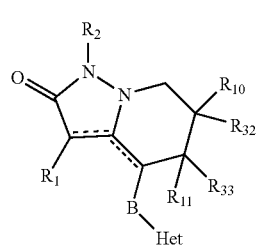
IIn

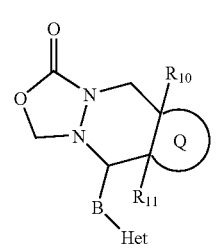
Io

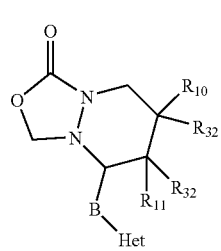
IIo

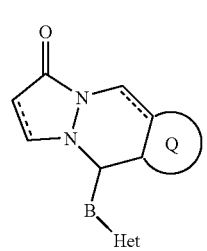
Ip

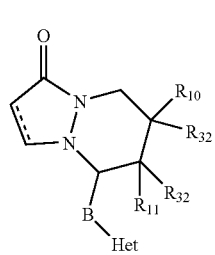
IIp

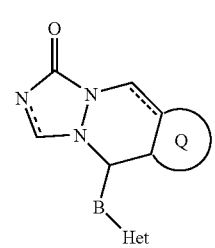
Iq

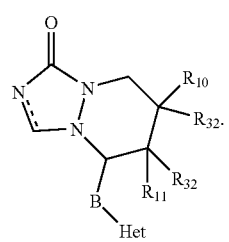
IIq

Another embodiment of the compound of formula I, wherein

A is

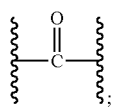

G is —O—, —(CR$^1$R$^2$)—, or NR$^1$;

U is CR$^1$R$^2$)—;

J is —(CR$^1$R$^2$)—;

K is CR$^1$ or —N—;

R$^{10}$ and R$^{11}$ are H;

R$^{32}$ and R$^{33}$ are combined to form a ring structure Q wherein Q is cyclohexyl;

B is —(CH$_2$)n$_4$CR$^{12}$=CR$^{12a}$(CH$_2$)n$_5$ wherein n$_4$ and n$_5$ are 0 and R$^{12}$ and R$^{12a}$ are Hydrogen;

Het is aryl, aryl substituted with W, heteroaryl, heteroaryl substituted with W;

W is aryl substituted with 1 to 3 moieties comprising halogen, alkyl, CF$_3$, CN, OH, or —Oalkyl.

Another embodiment of the compound of formula I, wherein

A is

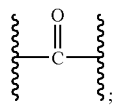

G is O—, —(CR¹R²) or NR¹;

U is —(CR¹R²)—;

J is —(CR¹R²)—;

K is CR¹ or —N—;

R³² and R³³ are combined to form a ring structure Q wherein Q is aryl;

B is —(CH₂)n₄CR¹²═CR¹²ᵃ(CH₂)n₅ wherein n₄ and n₅ are 0 and R¹² and R¹²ᵃ are Hydrogen;

Het is aryl, aryl substituted with W, heteroaryl, heteroaryl substituted with W;

W is aryl substituted with 1 to 3 moieties comprising halogen, alkyl, CF₃, CN, OH, or —Oalkyl.

Another embodiment of the compound of formula I, wherein

A is

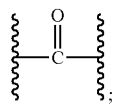

G is —O—

U is —(CH₂)—;

J is —(CH₂)—;

K is CH;

R¹⁰ and R¹¹ are H;

R³² and R³³ are combined to form a ring structure Q wherein Q is cyclohexyl;

B is —(CH₂)n₄CR¹²═CR¹²ᵃ(CH₂)n₅ wherein n₄ and n₅ are 0 and R¹² and R¹²ᵃ are Hydrogen;

Het is

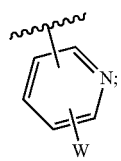

W is

or a pharmaceutically acceptable salt, solvate or ester thereof.

Another embodiment of the compound of formula I, wherein

A is

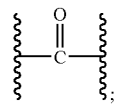

G is —O—

U is —(CH₂)—;

J is —(CH₂)—;

K is CH;

R³² and R³³ are combined to form a ring structure Q wherein Q is aryl;

B is —(CH₂)n₄CR¹²═CR¹²ᵃ(CH₂)n₅ wherein n₄ and n₅ are 0 and R¹² and R¹²ᵃ are Hydrogen;

Het is

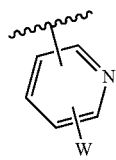

W is

Preferred embodiments of the compound of formula I, wherein

A is

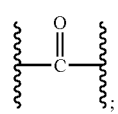

G is —O—

U is —(CH₂)—;

J is —(CH₂)—;

K is CH;

R¹⁰ and R¹¹ are H;

R³² and R³³ are combined to form a ring structure Q wherein Q is cyclohexyl;

B is —(CH₂)n₄CR¹²═CR¹²ᵃ(CH₂)n₅ wherein n₄ and n₅ are 0 and R¹² and R¹²ᵃ are Hydrogen;

Het is
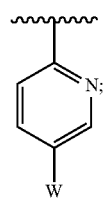
W is
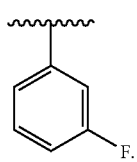
Additional preferred embodiment of the compound of formula I, wherein
A is
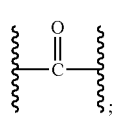
G is —O—
U is —(CH$_2$)—;
J is —(CH$_2$)—;
K is CH;
R$^{32}$ and R$^{33}$ are combined to form a ring structure Q wherein Q is phenyl;
B is —(CH$_2$)n$_4$CR$^{12}$=CR$^{12a}$(CH$_2$)n$_5$ wherein n$_4$ and n$_5$ are 0 and R$^{12}$ and R$^{12a}$ are Hydrogen;
Het is
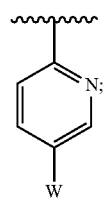
W is
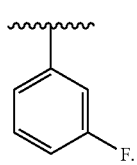
Still additional embodiments of the compounds of formula I are as follows:
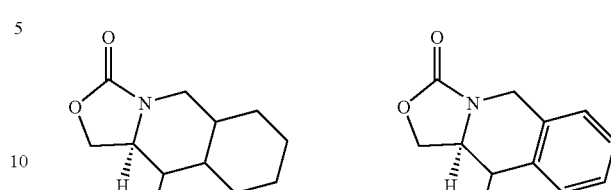
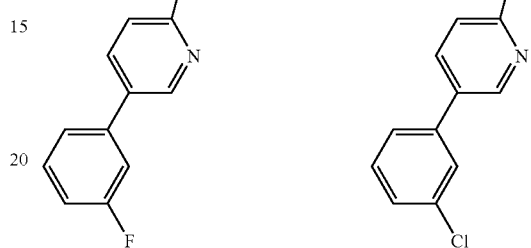
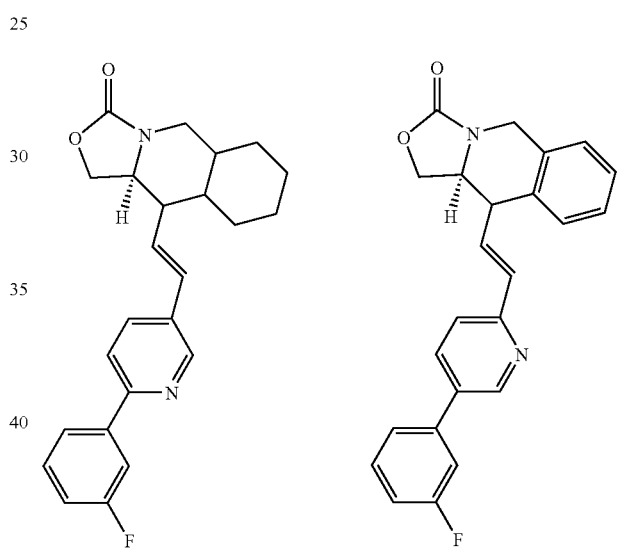
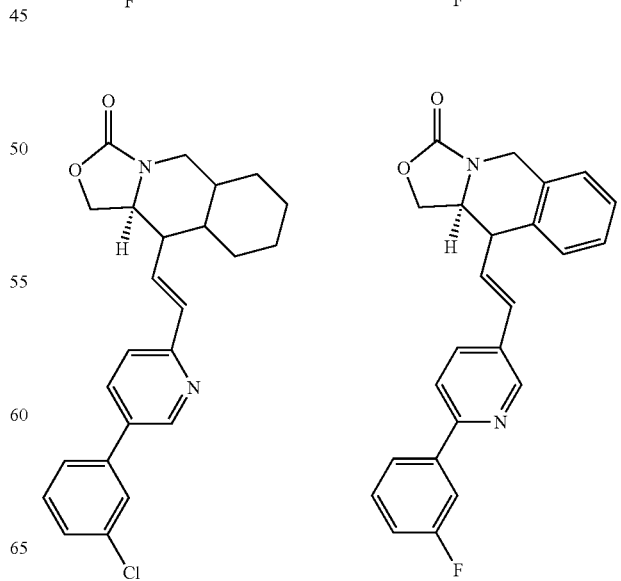

-continued
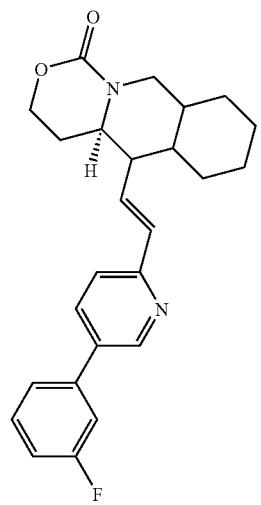 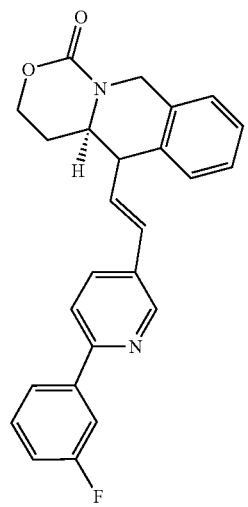 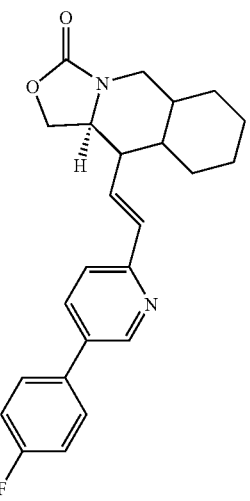 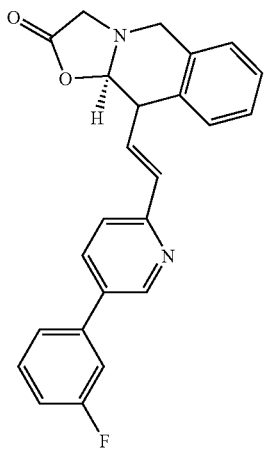
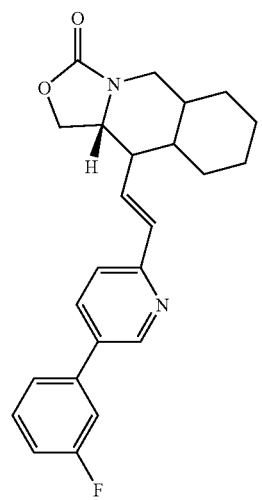 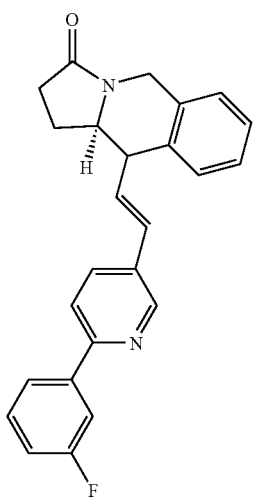 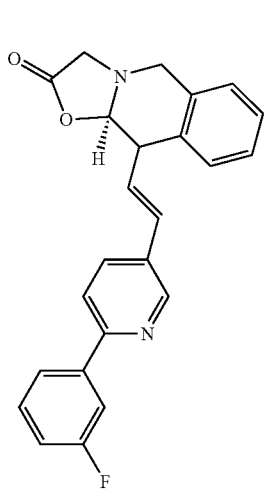
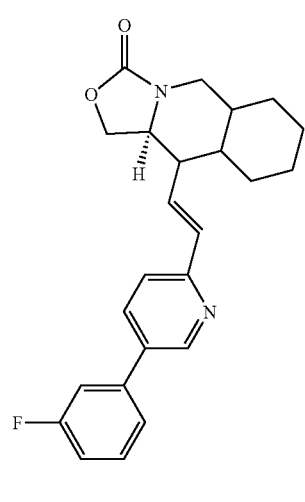 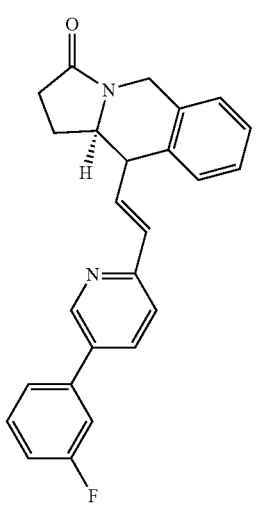 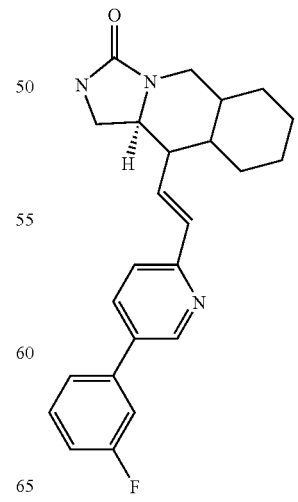 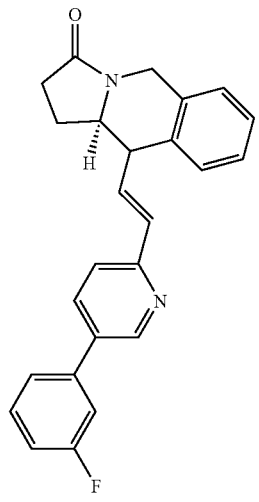

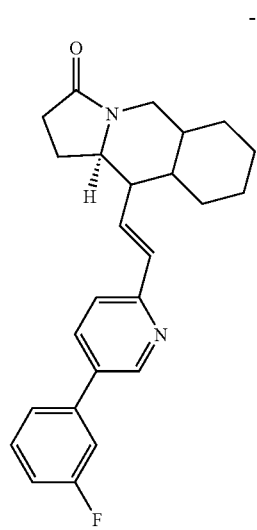
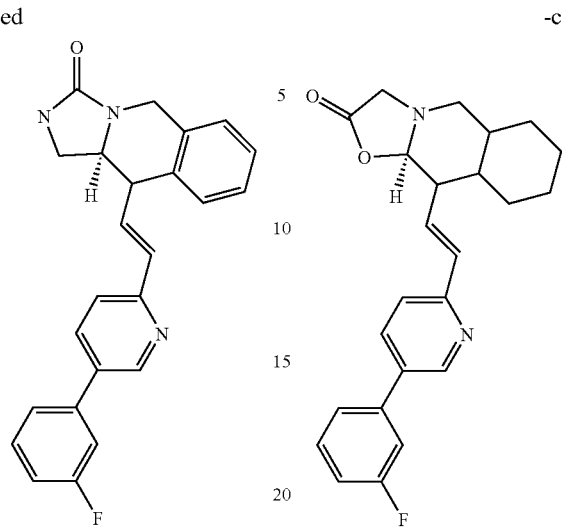
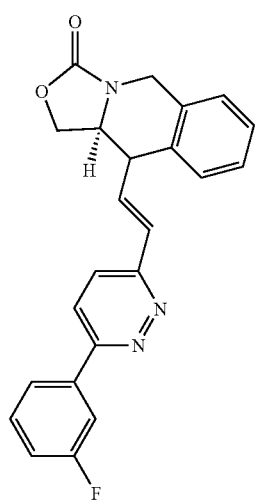
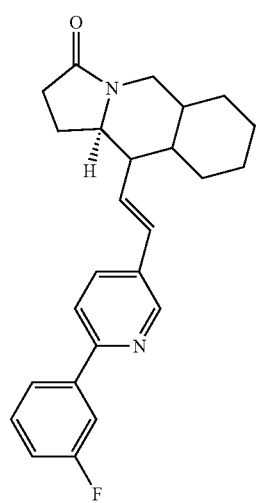
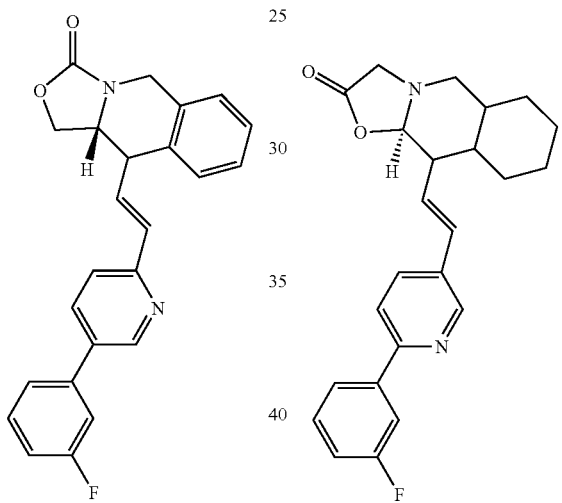
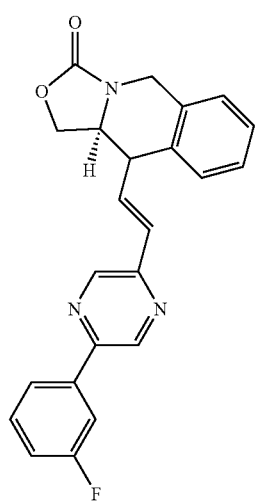
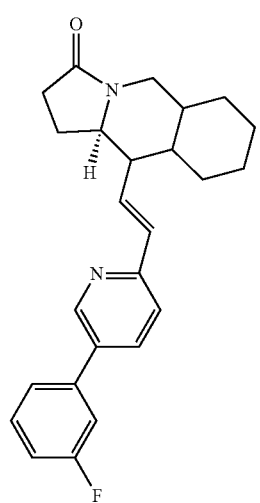
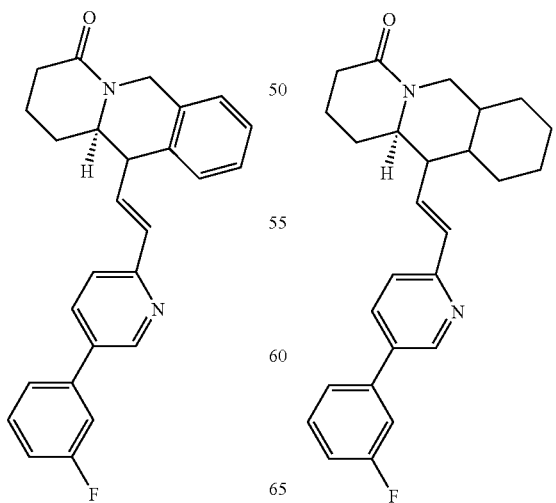
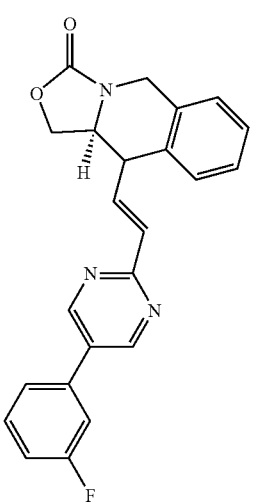

-continued
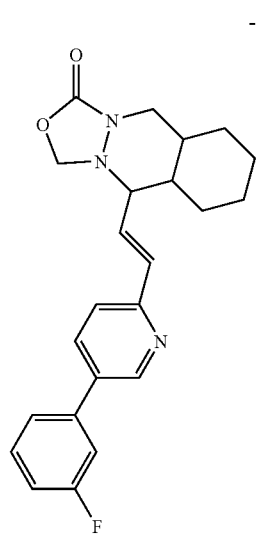
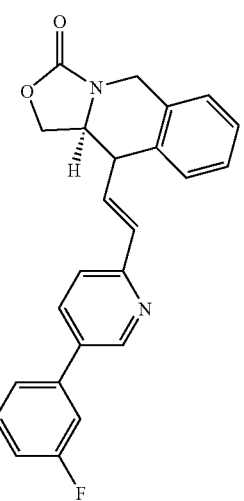
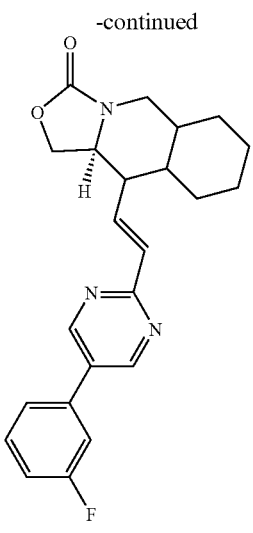
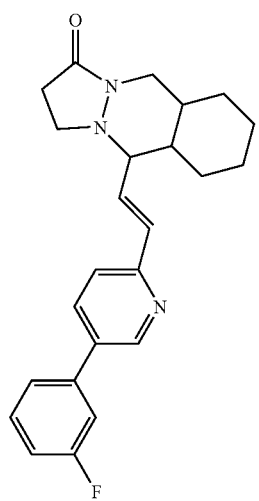
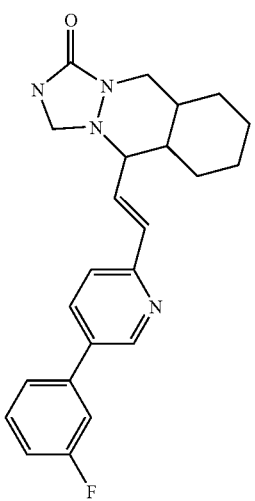
or
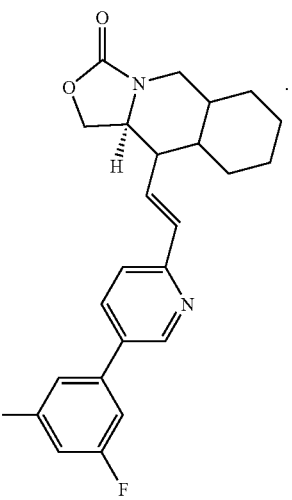
Other preferred embodiments of the compounds of formula I are as follows:
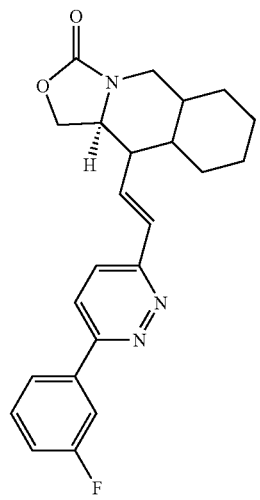
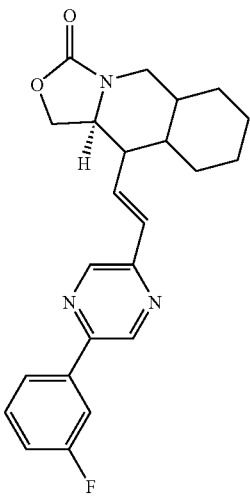
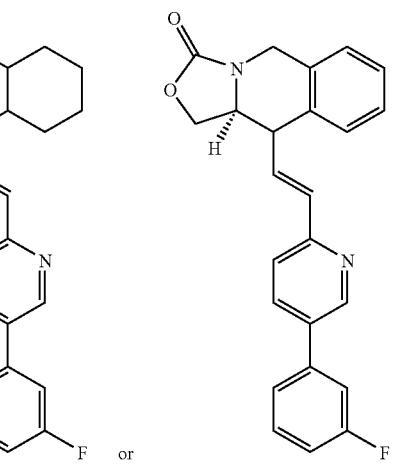
or a pharmaceutically acceptable salt, solvate or ester thereof.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazol[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

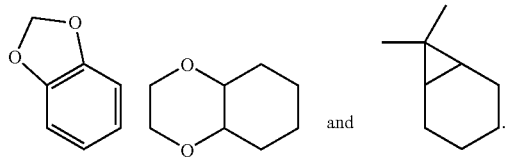

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazol idinyl, 1,4-dioxanyl, tetrahydrofuranyl, tetrahydrothiophenyl, lactam, lactone, and the like.

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, dihydroimidazole, dihydrooxazole, dihydrooxadiazole, dihydrothiazole, 3,4-dihydro-2H-pyran, dihydrofuranyl, fluorodihydrofuranyl, 7-oxabicyclo[2.2.1]heptenyl, dihydrothiophenyl, dihydrothiopyranyl, and the like.

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

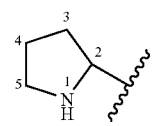

there is no —OH attached directly to carbons marked 2 and 5.

It should also be noted that tautomeric forms such as, for example, the moieties:

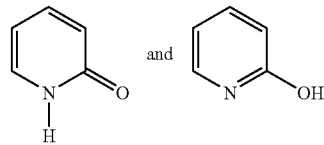

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl—O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula I or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-(C1-C2)alkyl and piperidino-, pyrrolidino- or morpholino($C_2$-$C_3$) alkyl, and the like.

Similarly, if a compound of Formula I contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate), and the like.

If a compound of Formula I incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —$C(OH)C(O)OY^1$ wherein $Y^1$ is H, ($C_1$-$C_6$)alkyl or benzyl, $C(OY^2)Y^3$ wherein $Y^2$ is ($C_1$-$C_4$) alkyl and $Y^3$ is ($C_1$-$C_6$)alkyl, carboxy($C_1$-$C_6$)alkyl, amino ($C_1$-$C_4$)alkyl or mono-N— or di-N,N—($C_1$-$C_6$)alkylaminoalkyl, —$C(Y^4)Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compound of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula I may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I and of the salts, solvates, esters and prodrugs of the compounds of Formula I are intended to be included in the present invention.

Pharmalogical properties of the compounds of this invention.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. thrombin receptor antagonists activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

The compounds of the invention may also be administered orally, intravenously, intranasally or subcutaneously.

The compounds of the invention may also comprise preparations which are in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents.

The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

When administering a combination therapy to a patient in need of such administration, the therapeutic agents in the combination, or a pharmaceutical composition or compositions comprising the therapeutic agents, may be administered in any order such as, for example, sequentially, concurrently, simultaneously and the like. The amounts of the various actives in such combination therapy may be different amounts (dosage amounts) or same amounts (dosage amounts). The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units. Thus, for illustration purposes, a compound of Formula I and an antiviral agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

As stated earlier, the invention includes tautomers, rotamers, enantiomers and other stereoisomers of the inventive compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Illustrative procedures are outlined in the following reaction schemes. The illustrations should not be construed to limit the scope of the invention which is defined in the appended claims. Alternative mechanistic pathways and analogous structures will be apparent to those skilled in the art.

EXPERIMENTAL EXAMPLES

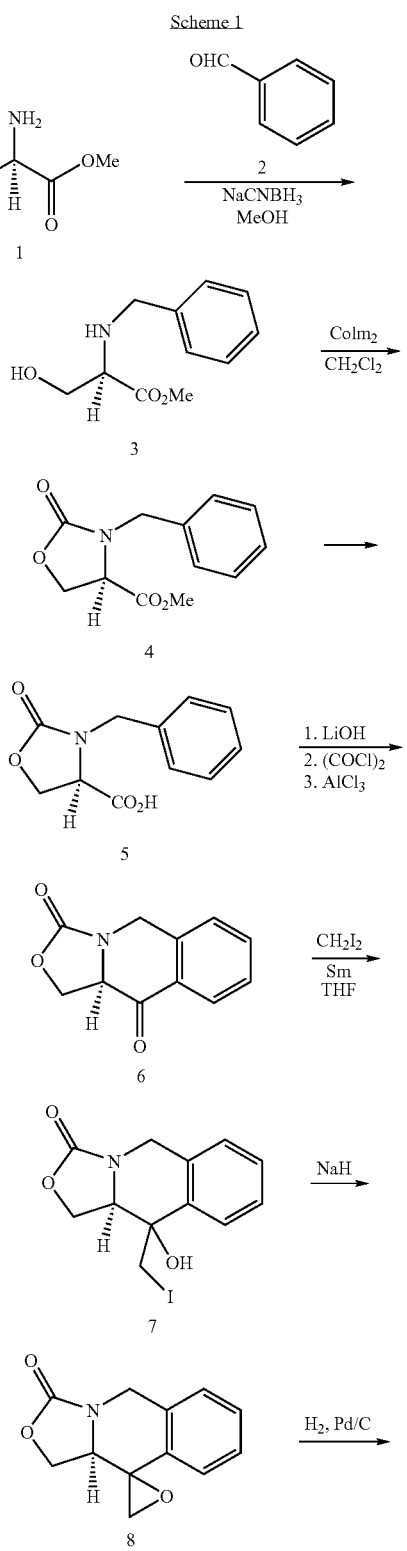

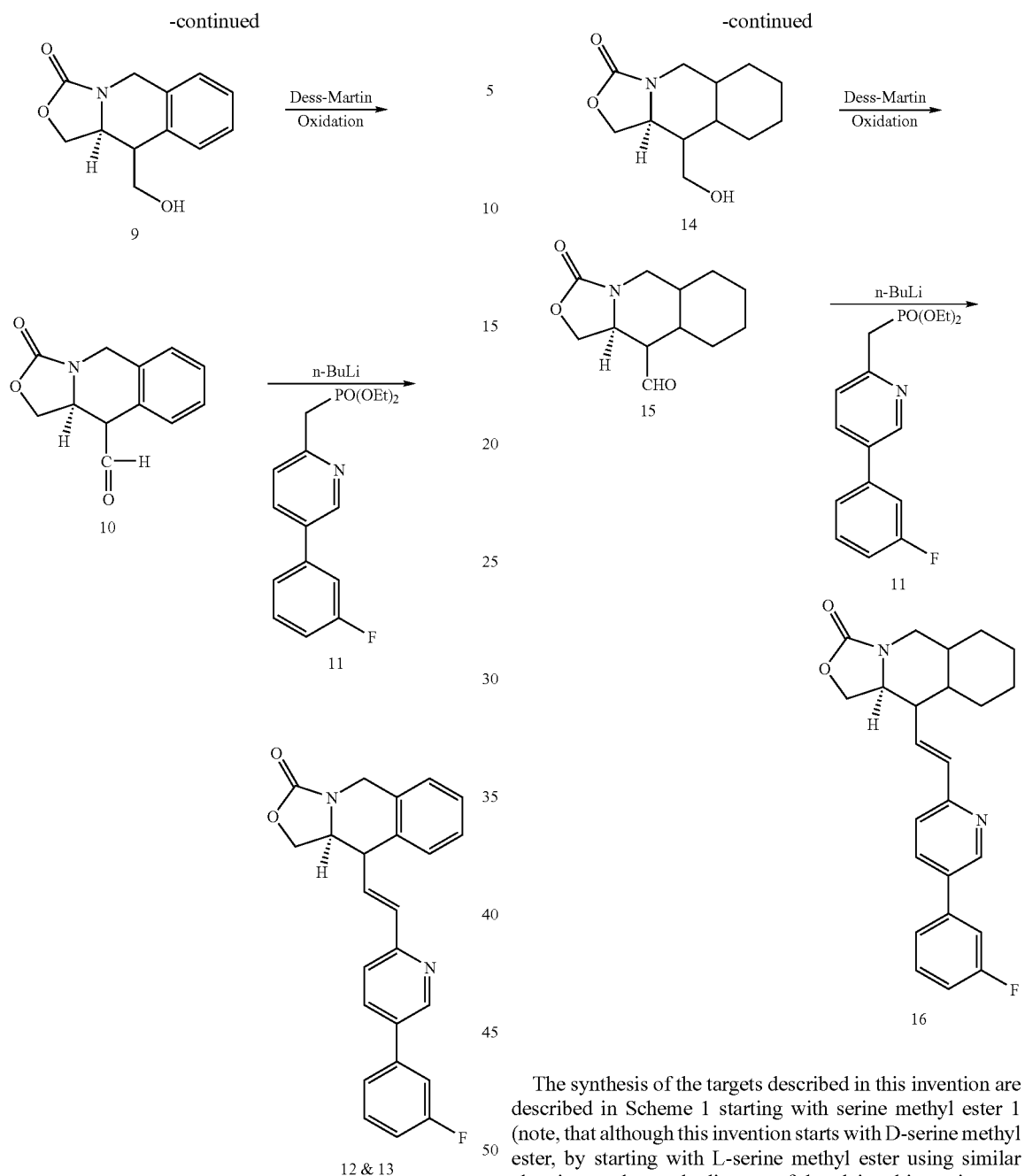

Alternatively:

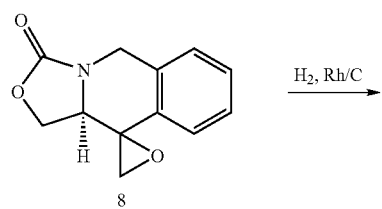

The synthesis of the targets described in this invention are described in Scheme 1 starting with serine methyl ester 1 (note, that although this invention starts with D-serine methyl ester, by starting with L-serine methyl ester using similar chemistry, other embodiments of the claimed invention can be derived), which upon reductive amination with benzaldehyde 2 gave the N-benzylated serine derivative 3. The N-benzylated serine derivative 3 was treated with carbonyldiimidazole to yield the carbonylimidazole methylester 4. The methylester of compound 4 was deprotected using $BBr_3$ followed by oxalyl chloride treatment, which mediated the formation of an acid chloride. Friedel crafts reaction of the acid chloride gave the tricyclic ketone 6. Treatment of 6 with samarium-diiodide resulted in the formation of an iodo tricyclic compound, which was reacted with base to yield an epoxide 8 which was subjected to hydrogenolytic ring opening followed by Dess-Martin oxidation to give the aldehyde 10. Condensation of the aldehyde 10 with the phosphonate 11 under Emmons-Wadsworth reaction conditions gave the olefin 12 & 13. Alternatively, 8 could be catalytically reduced

Example 1

Preparation of 10-{2-[5-(3-Fluoro-phenyl)-pyridin-2-yl]-vinyl}-1,5,10,10a-tetrahydro-oxazolo[3,4-b]isoquinolin-3-one Step 1:

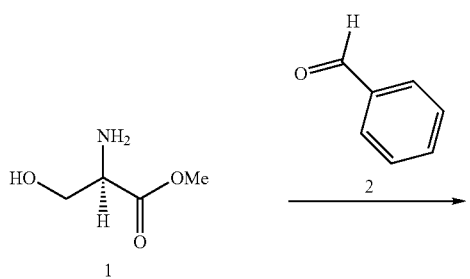

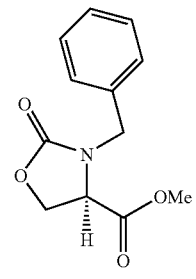

The methylester product of step 1 (3.41 g, 16.3 mmol) was dissolved in 80 mL of CH$_2$Cl$_2$ and 40 mL of ethyl acetate. 1,1-carbonyldiimidazole (3.5 g, 21.6 mmol) was added to the solution and stirred for 1 h at room temperature. Solvent was removed from the solution leaving a carbonylimidazole methylester that was further purified by column chromatography and produced a yield of 2.5 grams of carbonylimidazole methylester.

Step 3:

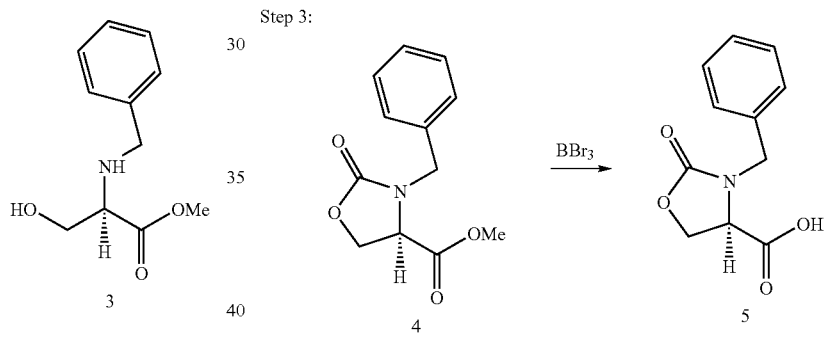

A mixture of D-Serine (7.71 g, 49 mmol), benzaldehyde (7.6 mL, 74 mmol) and NaCNBH$_3$ (9.1 g, 147 mmol) was stirred over the weekend in MeOH (50 mL). The mixture was poured into 200 mL of ether, washed with saturated NaHCO$_3$, and dried with NaHCO$_3$. The solvent was removed leaving a methylester (compound 3) that was purified using column chromatography, resulting in a yield of 3.41 g of the methylester.

The carbonylimidazole methyl ester product of step 2 (2.3 g, 9.78 mmol) was dissolved in 10 mL of CH$_2$Cl$_2$ followed by the addition of 1N BBr3 at 0° C. The solution was stirred at room temperature overnight then poured into water and extracted with ethyl acetate. The extract was dried with MgSO$_4$ then the solvent was removed to yield 2.1 g. of a crude carboxylic acid (compound 5).

Step 2:

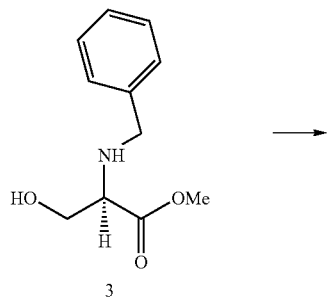

Step 4:

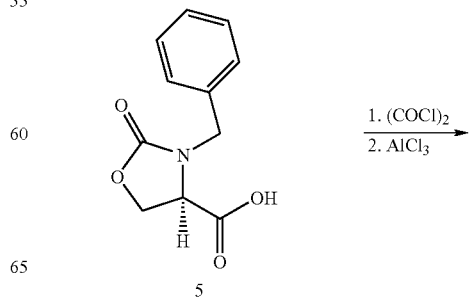

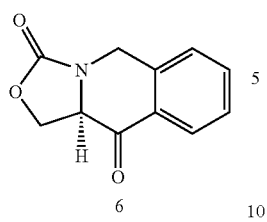

5

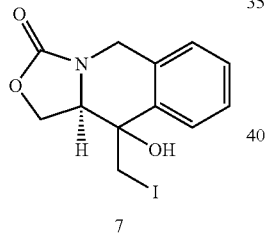

6

The crude carboxylic acid (1 g, 4.5 mmol) was dissolved in 15 ml of CH$_2$Cl$_2$ and cooled down to 0° C. Oxalyl chloride (1 mL, 9.2 mmol) was added to the solution and stirred at room temperature for 2 h. The solvent was removed leaving a crude product. The crude product was added to 20 ml of CH$_2$Cl$_2$ followed by the addition of AlCl$_3$ (1.3 g, 10 mmol). The reaction mixture was heated to reflux for 2 h under nitrogen then cooled to room temperature and diluted with CH$_2$Cl$_2$. The methylene chloride diluent was washed with water, dried with MgSO$_4$, and purified by column chromatography to yield 0.34 g of a tricyclic ketone (compound 6).

Step 5:

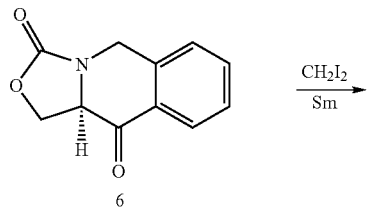

The tricyclic ketone (compound 6) (290 mg, 1.4 mmol) and CH$_2$I$_2$ in THF (10 mL) were added dropwise to a Samarian solution prepared by suspending samarium (1.3 g, 8.55 mmol) in dry THF (6 mL) under N$_2$ at 0° C. The mixture was stirred at 0° C. for 2 h then washed with 1N HCl and dried with MgSO$_4$. The mixture was then purified by column chromatography to afford 73 mg of an iodo tricyclic compound (compound 7).

Step 6:

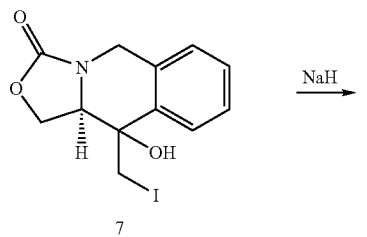

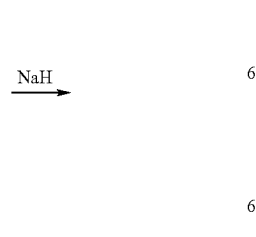

8

The iodomethyl tricyclic derivative (Compound 7) (320 mg, 0.93 mmol) was dissolved in THF (5 mL) at room temperature under N$_2$ and 55% NaH (166 mg, 2.4 mmol) was added. The reaction mixture was stirred overnight resulting in a tricyclic epoxide that was further purified by column chromatography to yield 150 mg of the tricyclic epoxide (compound 8).

Step 7:

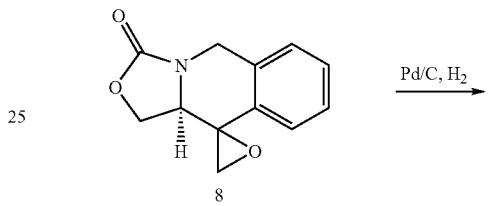

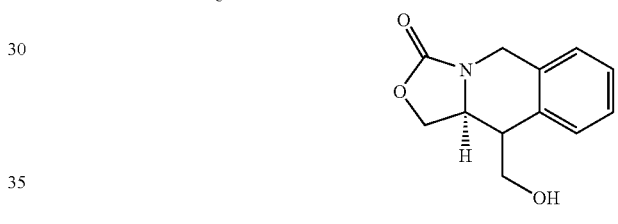

The tricyclic epoxide (compound 8) (150 mg, 0.69 mmol) was hydrogenated in ethyl acetate (8 mL) with 10% Pd/C (200 mg) for 4 h at 1 atm (~14 psi) H$_2$ resulting in a hydroxymethyl tricyclic compound (compound 9) that was further purified by column chromatography to yield 100 mg of compound 9.

Step 8:

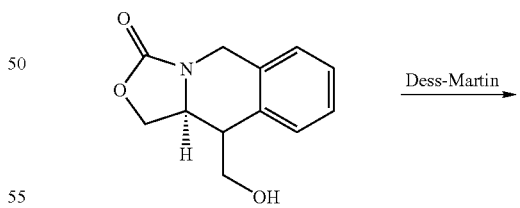

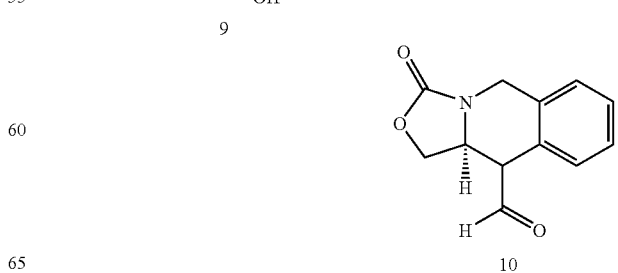

The hydroxymethyl tricyclic compound (Compound 9) (44 mg, 0.2 mmol) was added to CH$_2$Cl$_2$ (4 mL) followed by the addition of Dess-Martin reagent (136 mg, 0.32 mmol) and NaHCO$_3$ (27 mg, 0.32 mmol). The reaction mixture was stirred at room temperature for 2 h 40 min and combined with a solution of saturated Na$_2$S$_2$O$_3$ (20 mL). The mixture was then extracted with CH$_2$Cl$_2$ and dried with MgSO$_4$. The solvent was removed to afford the crude tricyclic aldehyde (compound 10) to be used in the next step without purification.

Step 9:

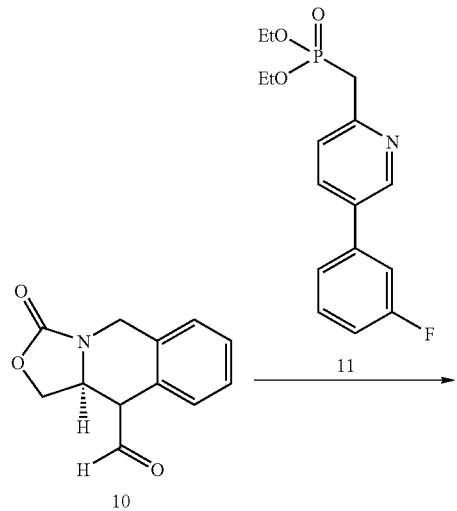

The crude tricyclic aldehyde (compound 10) from step 8 in THF (3 mL) was added to a reaction mixture that was prepared by cooling a solution of [5-(3-Fluoro-phenyl)-pyridin-2-ylmethyl]-phosphonic acid diethyl ester (compound 11) (162 mg, 0.5 mmol) in THF (3 mL) to 0° C. using an ice bath then adding 2.5 M n-BuLi (0.2 mL, 0.5 mmol) and stirring it at 0° C. for 15 min followed by addition of titanium tetraisopropoxide (Ti(O-iPr)$_4$) (142 mg, 0.5 mol) then warming the reaction mixture to room temperature. The reaction mixture, now containing the crude tricyclic aldehyde (compound 10) was stirred at room temperature overnight, diluted with ethyl acetate (50 mL), washed with saturated K—Na-tartrate, dried with MgSO$_4$ and separated by column chromatography, which afforded target compounds 12 and 13, which are isomeric at the benzylic carbon. Target compounds 12: 387 (M+1); Thrombin Receptor Angagonist Activity: 27% inhibition at 1 µM and 13: 387 (M+1); Thrombin Receptor Antagonist Activity: 15% inhibition at 1 µM.

Example 2

Preparation of 10-{(2-[5-(3-Fluoro-phenyl)-pyridin-2-yl]-vinyl}-decahydro-oxazolo[3,4-b]isoquinolin-3-one Step 7b:

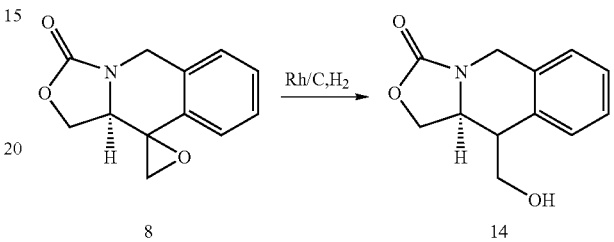

Alternatively, the tricyclic epoxide (compound 8) (40 mg, 0.18 mmol) was dissolved in methanol (5 mL) along with 200 mg of 5% R$^h$/C catalyst. Acetic acid (0.2 mL) was added and the reaction mixture was hydrogenated at medium pressure (45-50 psi) overnight. The catalyst was filtered from the reaction mixture and the solvent was removed to yield the hydroxy-methyl tricyclic compound (compound 14) (35 mg).

Step 8b:

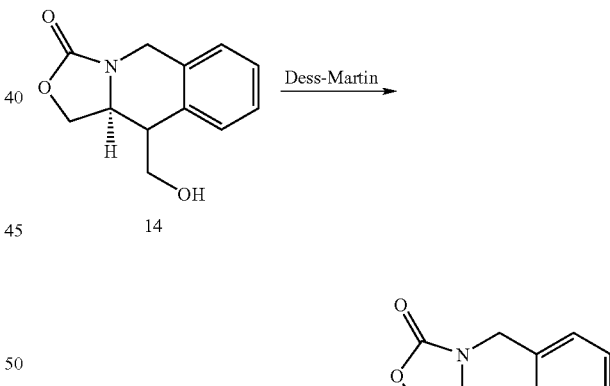

The hydroxy-methyl tricyclic compound (compound 14) (60 mg, 0.27 mmol) was dissolved in CH$_2$Cl$_2$ (4 mL) followed by the addition of Dess-Martin reagent (136 mg) and NaHCO$_3$ (27 mg). The reaction mixture was stirred for 2.5 hours at room temperature after which, a solution of saturated Na$_2$S$_2$O$_3$ was added. The reaction mixture was stirred for 15 min. then extracted with CH$_2$Cl$_2$ and dried with MgSO$_4$. Next, the mixture was purified by column chromatography to yield 16 mg of the tricyclic aldehyde (compound 15).

Step 9b:

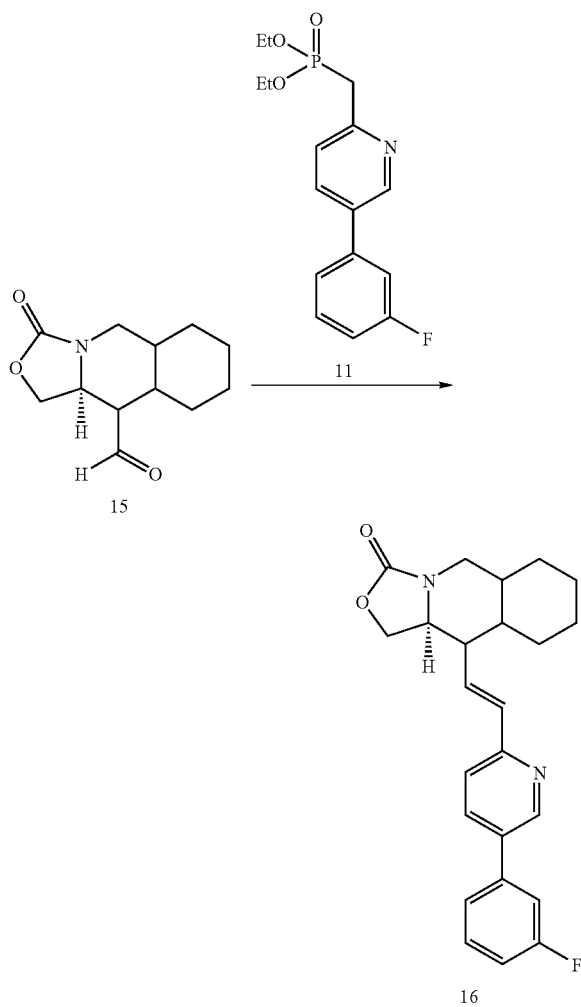

The crude tricyclic aldehyde (compound 15) from step 8b in THF (3 mL) was added to a reaction mixture that was prepared by cooling a solution of [5-(3-Fluoro-phenyl)-pyridin-2-ylmethyl]-phosphonic acid diethyl ester (compound 11) (162 mg, 0.5 mmol) in THF (3 mL) to 0° C. using an ice bath then adding 2.5 M n-BuLi (0.2 mL, 0.5 mmol) and stirring it at 0° C. for 15 min followed by addition of titanium tetraisopropoxide (Ti(O-iPr)$_4$) (142 mg, 0.5 mol) and warming the reaction mixture to room temperature. The reaction mixture, now containing the crude tricyclic aldehyde (compound 10), was stirred at room temperature overnight, diluted with ethyl acetate (50 mL), washed with saturated K—Na-tartrate, dried with MgSO$_4$ and separated by column chromatography, which afforded 25 mg of product (compound 16). 16: 393 (M+1), (Target compound 16 (Thrombin Receptor Ki=12 nM)).

Further embodiments of the invention encompass the administration of compounds of Formula I along with at least one additional cardiovascular agent. The contemplated additional cardiovascular agent is one that differs in either atomic make up or arrangement from the compounds of Formula I. Additional cardiovascular agents that can be used in combination with the novel compounds of this invention include drugs, which have anti-thrombotic, anti-platelet aggregation, antiatherosclerotic, antirestenotic and/or anti-coagulant activity. Such drugs are useful in treating thrombosis-related diseases including thrombosis, atherosclerosis, restenosis, hypertension, angina pectoris, angiogenesis related disorders, arrhythmia, a cardiovascular or circulatory disease or condition, heart failure, myocardial infarction, glomerulonephritis, thrombotic stroke, thromboembolytic stroke, peripheral vascular diseases, cerebral ischemia, rheumatoid arthritis, rheumatism, astrogliosis, a fibrotic disorder of the liver, kidney, lung or intestinal tract, systemic lupus erythematosus, multiple sclerosis, osteoporosis, glomerulonephritis, renal disease, acute renal failure, chronic renal failure, renal vascular homeostasis, renal ischemia, bladder inflammation, diabetes, diabetic neuropathy, cerebral stroke, cerebral ischemia, nephritis, cancer, melanoma, renal cell carcinoma, neuropathy and/or malignant tumors, neurodegenerative and/or neurotoxic diseases, conditions, or injuries, inflammation, asthma, glaucoma, macular degeneration, psoriasis, endothelial dysfunction disorders of the liver, kidney or lung inflammatory disorders of the lungs and gastrointestinal tract, respiratory tract disease or condition, radiation fibrosis, endothelial dysfunction, periodontal diseases or wounds or a spinal cord injury, or a symptom or result thereof, as well as other disorders in which thrombin and its receptor play a pathological role. Suitable cardiovascular agents are selected from the group consisting of thromboxane A2 biosynthesis inhibitors such as aspirin; thromboxane antagonists such as seratrodast, picotamide and ramatroban; adenosine diphosphate (ADP) inhibitors such as clopidogrel; cyclooxygenase inhibitors such as aspirin, meloxicam, rofecoxib and celecoxib; angiotensin antagonists such as valsartan, telmisartan, candesartran, irbesartran, losartan and eprosartan; endothelin antagonists such as tezosentan; phosphodiesterase inhibitors such as milrinoone and enoximone; angiotensin converting enzyme (ACE) inhibitors such as captopril, enalapril, enalprilat, spirapril, quinapril, perindopril, ramipril, fosinopril, trandolapril, lisinopril, moexipril and benazapril; neutral endopeptidase inhibitors such as candoxatril and ecadotril; anticoagulants such as ximelagatran, fondaparin and enoxaparin; diuretics such as chlorothiazide, hydrochlorothiazide, ethacrynic acid, furosemide and amiloride; platelet aggregation inhibitors such as abciximab and eptifibatide; and GP IIb/IIIa antagonists.

Preferred types of drugs for use in combination with the novel compounds of this invention are thromboxane A2 biosynthesis inhibitors, GP IIb/IIIa antagonists, thromboxane antagonists, adenosine diphosphate inhibitors, cyclooxygenase inhibitors, angiotensin antagonists, endothelin antagonists, angiotensin converting enzyme inhibitors, neutral endopeptidase inhibitors, anticoagulants, diuretics, and platelet aggregation inhibitors. Especially preferred for use in the combinations are aspirin, cangrelor and/or clopidogrel bisulfate.

When the invention comprises a combination of compounds of Formula I and another cardiovascular agent, the two active components may be co-administered simultaneously or sequentially, or a single pharmaceutical composition comprising compounds of Formula I and another cardiovascular agent in a pharmaceutically acceptable carrier can be administered. The components of the combination can be administered individually or together in any conventional dosage form such as capsule, tablet, powder, cachet, suspension, solution, suppository, nasal spray, etc. The dosage of the cardiovascular agent can be determined from published material, and may range from 1 to 1000 mg per dose.

In this specification, the term "at least one compound of Formula I" means that one to three different compounds of Formula I may be used in a pharmaceutical composition or method of treatment. Preferably one compound of Formula I is used. Similarly, the term "one or more additional cardiovascular agents" means that one to three additional drugs may be administered in combination with a compound of Formula I; preferably, one additional compound is administered in combination with a compound of Formula I. The additional cardiovascular agents can be administered sequentially or simultaneously with reference to the compounds of Formula I.

When separate compounds of Formula I and the other cardiovascular agents are to be administered as separate compositions, they can be provided in a kit comprising in a single package, one container comprising a compounds of Formula I in a pharmaceutically acceptable carrier, and a separate container comprising another cardiovascular agent in a pharmaceutically acceptable carrier, with the compounds of Formula I and the other cardiovascular agent being present in amounts such that the combination is therapeutically effective. A kit is advantageous for administering a combination when, for example, the components must be administered at different time intervals or when they are in different dosage forms.

The activity of the compounds of formula I can be determined by the following procedures.

In Vitro Testing Procedure for Thrombin Receptor Antagonists:

Preparation of [$^3$H]ha TRAP

A(pF-F)R(ChA)(hR)(I$_2$—Y)—NH$_2$ (1.03 mg) and 10% Pd/C (5.07 mg) were suspended in DMF (250 µl) and diisopropylethylamine (10 µl). The vessel was attached to the tritium line, frozen in liquid nitrogen and evacuated. Tritium gas (342 mCi) was then added to the flask, which was stirred at room temperature for 2 hours. At the completion of the reaction, the excess tritium was removed and the reacted peptide solution was diluted with DMF (0.5 ml) and filtered to remove the catalyst. The collected DMF solution of the crude peptide was diluted with water and freeze dried to remove the labile tritium. The solid peptide was redissolved in water and the freeze drying process repeated. The tritiated peptide ([$^3$H]haTRAP) was dissolved in 0.5 ml of 0.1% aqueous TFA and purified by HPLC using the following conditions: column, Vydac™ C18, 25 cm×9.4 mm I.D.; mobile phase, (A) 0.1% TFA in water, (B) 0.1% TFA in CH$_3$CN; gradient, (A/B) from 100/0 to 40/60 over 30 min; flow rate, 5 ml/min; detection, UV at 215 nm. The radiochemical purity of [$^3$H]haTRAP was 99% as analyzed by HPLC. A batch of 14.9 mCi at a specific activity of 18.4 Ci/mmol was obtained.

Preparation of Platelet Membranes

Platelet membranes were prepared using a modification of the method of Natarajan et al. (Natarajan et al, Int. J. Peptide Protein Res. 45:145-151 (1995)) from 20 units of platelet concentrates obtained from the North Jersey Blood Center (East Orange, N.J.) within 48 hours of collection. All steps were carried out at 4° C. under approved biohazard safety conditions. Platelets were centrifuged at 100×g for 20 minutes at 4° C. to remove red cells. The supernatants were decanted and centrifuged at 3000×g for 15 minutes to pellet platelets. Platelets were re-suspended in 10 mM Tris-HCl, pH 7.5, 150 mM NaCl, 5 mM EDTA, to a total volume of 200 ml and centrifuged at 4400×g for 10 minutes. This step was repeated two additional times. Platelets were re-suspended in 5 mM Tris-HCl, pH 7.5, 5 mM EDTA to a final volume of approximately 30 ml and were homogenized with 20 strokes in a Dounce™ homogenizer. Membranes were pelleted at 41,000×g, re-suspended in 40-50 ml 20 mM Tris-HCl, pH 7.5, 1 mM EDTA, 0.1 mM dithiothreitol, and 10 ml aliquots were frozen in liquid N$_2$ and stored at −80° C. To complete membrane preparation, aliquots were thawed, pooled, and homogenized with 5 strokes of a Dounce homogenizer. Membranes were pelleted and washed 3 times in 10 mM triethanolamine-HCl, pH 7.4, 5 mM EDTA, and re-suspended in 20-25 ml 50 mM Tris-HCl, pH 7.5, 10 mM MgCl$_2$, 1 mM EGTA, and 1% DMSO. Aliquots of membranes were frozen in liquid N$_2$ and stored at −80° C. Membranes were stable for at least 3 months. 20 units of platelet concentrates typically yielded 250 mg of membrane protein. Protein concentration was determined by a Lowry assay (Lowry et al., J. Biol. Chem., 193:265-275 (1951)).

High Throughput Thrombin Receptor Radioligand Binding Assay

Thrombin receptor antagonists were screened using a modification of the thrombin receptor radioligand binding assay of Ahn et al. (Ahn et al., Mol. Pharmacol., 51:350-356 (1997)). The assay was performed in 96 well Nunc plates (Cat. No. 269620) at a final assay volume of 200 µl. Platelet membranes and [$^3$H]haTRAP were diluted to 0.4 mg/ml and 22.2 nM, respectively, in binding buffer (50 mM Tris-HCl, pH 7.5, 10 mM MgCl$_2$, 1 mM EGTA, 0.1% BSA). Stock solutions (10 mM in 100% DMSO) of test compounds were further diluted in 100% DMSO. Unless otherwise indicated, 10 µl of diluted compound solutions and 90 µl of radioligand (a final concentration of 10 nM in 5% DMSO) were added to each well, and the reaction was started by the addition of 100 µl of membranes (40 µg protein/well). The binding was not significantly inhibited by 5% DMSO. Compounds were tested at three concentrations (0.1, 1 and 10 µM). The plates were covered and vortex-mixed gently on a Lab-Line™ Titer Plate Shaker for 1 hour at room temperature. Packard UniFilter™ GF/C filter plates were soaked for at least 1 hour in 0.1% polyethyleneimine. The incubated membranes were harvested using a Packard FilterMate™ Universal Harvester and were rapidly washed four times with 300 µl ice cold 50 mM Tris-HCl, pH 7.5, 10 mM MgCl$_2$, 1 mM EGTA. MicroScint™ 20 scintillation cocktail (25 µl) was added to each well, and the plates were counted in a Packard TopCount™ Microplate Scintillation Counter. The specific binding was defined as the total binding minus the nonspecific binding observed in the presence of excess (50 µM) unlabeled haTRAP. The % inhibition by a compound of [$^3$H]haTRAP binding to thrombin receptors was calculated from the following relationship:

$$\% \text{ Inhibition} = \frac{\text{Total binding} - \text{Binding in the presence of a test compound}}{\text{Total binding} - \text{Nonspecific binding}} \times 100$$

Materials

A(pF-F)R(ChA)(hR)Y—NH$_2$ and A(pF-F)R(ChA)(hR)(I$_2$—Y)—NH$_2$, were custom synthesized by AnaSpec Inc. (San Jose, Calif.). The purity of these peptides was >95%. Tritium gas (97%) was purchased from EG&G Mound, Miamisburg, Ohio. The gas was subsequently loaded and stored on an IN/US Systems Inc. Trisorber. MicroScint™ 20 scintillation cocktail was obtained from Packard Instrument Co.

Cannabinoid CB$_2$ Receptor Binding Assay

Binding to the human cannabinoid CB$_2$ receptor was carried out using the procedure of Showalter, et al. (1996, J. Pharmacol Exp Ther. 278(3), 989-99), with minor modifications. All assays were carried out in a final volume of 100 ul. Test compounds were re-suspended to 10 mM in DMSO, then serially diluted in 50 mM Tris, pH 7.1, 3 mM MgCl$_2$, 1 mM EDTA, 50% DMSO. Aliquots (10 ul) of each diluted sample were then transferred into individual wells of a 96-well microtiter plate. Membranes from human CB$_2$ transfected CHO/Ki cells (Receptor Biology, Inc) were re-suspended in binding buffer (50 mM Tris, pH 7.1, 3 mM MgCl$_2$, 1 mM EDTA, 0.1% fatty acid free bovine serum albumin), then added to the binding reaction (~15 ug in 50 ul per assay). The reactions were initiated with the addition of [$^3$H] CP-55, 940 diluted in binding buffer (specific activity=180 Ci/mmol; New England Nuclear, Boston, Mass.). The final ligand concentration in the binding reaction was 0.48 nM. Following incubation at room temperature for 2 hours, membranes were harvested by filtration through pretreated (0.5% polyethylenimine; Sigma P-3143) GF-C filter plates (Unifilter-96, Packard) using a TomTec™ Mach 3U 96-well cell harvester (Hamden, Conn.). Plates were washed 10 times in 100 ul binding buffer, and the membranes allowed to air dry. Radioactivity on membranes was quantitated following addition of Packard Omniscint™ 20 scintillation fluid using a TopCount™ NXT Microplate Scintillation and Luminescence Counter (Packard, Meriden, Conn.). Non-linear regression analysis was performed using Prism™ 20b. (GraphPad Software, San Diego, Calif.).

Using the test procedures described above, representative compounds of formula I were found to have thrombin receptor $IC_{50}$ values (i.e., the concentration at which a 50% inhibition of thrombin receptor was observed) of 1 to 1000 nM, preferably 1-100 nM, more preferably 1-20 nM. $CB_2$ Ki values range from 1 to 1000 nM, preferably 1-200 nM, more preferably 1-100 nM.

What is claimed is:

1. A compound of the formula

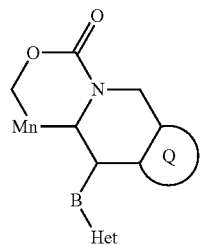

Ib or a pharmaceutically acceptable salt of said compound wherein:

B is —CH═CH—;
M is —C($R^1$)($R^2$)—;
n is 0 or 1;
Het is a mono heteroaromatic group of 5 to 6 atoms comprised of 2 to 5 carbon atoms and 1 to 2 heteroatoms independently selected from the group consisting of N, O and S, with the proviso that there are no adjacent oxygen or sulfur atoms present in the heteroaromatic group, wherein a ring nitrogen can form an N-oxide or a quaternary group with an alkyl group, wherein Het is attached to B by a carbon atom ring member of the Het group, and wherein the Het group is substituted by 1 moiety, W,
wherein W is aryl or aryl substituted by 1 to 3 substituents independently selected from the group consisting of alkyl, halogen, -Oalkyl, —CN, —$CF_3$, and —OH;
$R^1$ and $R^2$ are independently hydrogen or alkyl; and
Q is

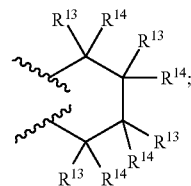

wherein each $R^{13}$ and R14 are hydrogen.

2. A compound of claim 1 or a pharmaceutically acceptable salt thereof wherein said compound is of the formula:

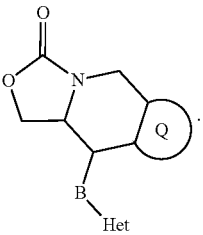

3. A compound of claim 1 or a pharmaceutically acceptable salt thereof wherein:

Het is

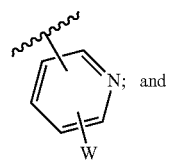

W is

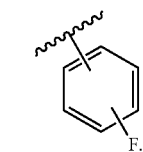

4. A compound of claim 1 or a pharmaceutically acceptable salt thereof wherein:

Het is

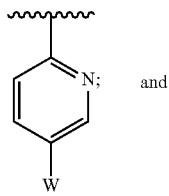

W is

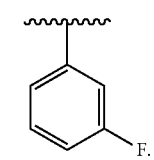

5. A compound of selected from the group consisting of:

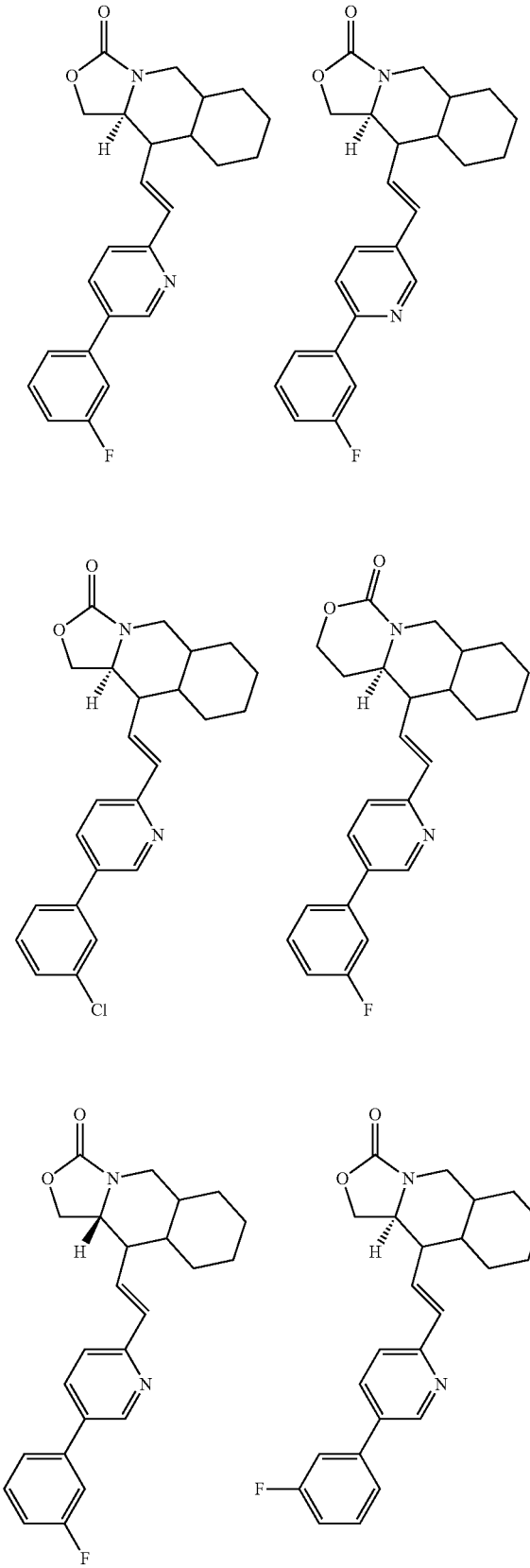

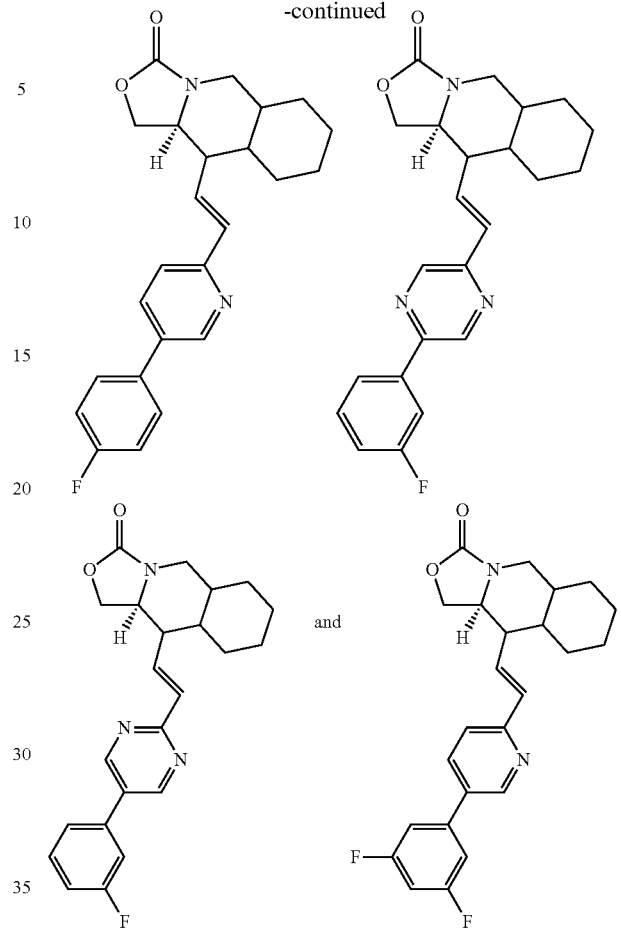

or pharmaceutically acceptable salt or thereof.

6. A compound of claim 1 which has the following formula:

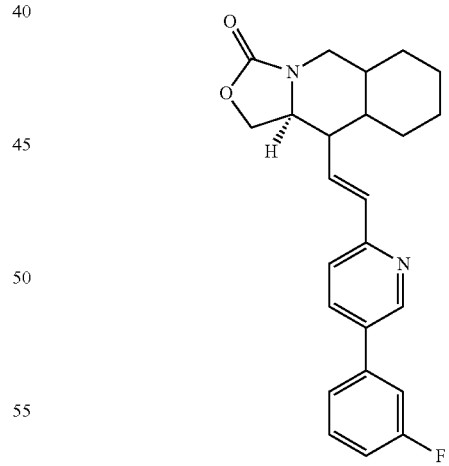

or a pharmaceutically acceptable salt thereof.

7. A pharmaceutical composition comprising an effective amount of at least one compound of claim 1 or a pharmaceutically acceptable salt thereof and a pharmaceutically acceptable carrier.

8. A pharmaceutical composition comprising an effective amount of at least one compound of claim 5 or a pharmaceutically acceptable salt thereof and a pharmaceutical carrier.

* * * * *